(12) United States Patent
Nicolaides et al.

(10) Patent No.: US 12,416,642 B2
(45) Date of Patent: Sep. 16, 2025

(54) COMPOSITION AND METHODS FOR MEASURING ANTIBODY DYNAMICS

(71) Applicant: Navrogen, Glen Mills, PA (US)

(72) Inventors: Nicholas C. Nicolaides, Glen Mills, PA (US); Luigi Grasso, Bryn Mawr, PA (US)

(73) Assignee: Navrogen, Inc., Glen Mills, PA (US)

( * ) Notice: Subject to any disclaimer, the term of this patent is extended or adjusted under 35 U.S.C. 154(b) by 1193 days.

(21) Appl. No.: 17/277,098

(22) PCT Filed: Sep. 18, 2019

(86) PCT No.: PCT/US2019/051706
§ 371 (c)(1),
(2) Date: Mar. 17, 2021

(87) PCT Pub. No.: WO2020/068511
PCT Pub. Date: Apr. 2, 2020

(65) Prior Publication Data
US 2021/0285960 A1  Sep. 16, 2021

Related U.S. Application Data

(60) Provisional application No. 62/737,414, filed on Sep. 27, 2018.

(51) Int. Cl.
*G01N 33/68* (2006.01)
*C07K 16/00* (2006.01)
(Continued)

(52) U.S. Cl.
CPC ......... *G01N 33/6854* (2013.01); *C07K 16/00* (2013.01); *C07K 16/2887* (2013.01);
(Continued)

(58) Field of Classification Search
CPC ............. G01N 33/6854; G01N 33/542; G01N 2500/02; G01N 2500/20; G01N 33/6857;
(Continued)

(56) References Cited

U.S. PATENT DOCUMENTS 4,444,879 A * 4/1984 Foster ................ G01N 33/6854
435/805
2008/0064025 A1 3/2008 Su
(Continued)

FOREIGN PATENT DOCUMENTS

JP 2015500459 A 1/2015
WO 02056024 A2 7/2002
(Continued)

OTHER PUBLICATIONS

Wang J, Qiu L, Wang C, Zhang Y, Li J, Xia J, Jiang P. Probing antigen-antibody interaction using fluorescence coupled capillary electrophoresis. Int J Mol Sci. Sep. 17, 2013;14(9):19146-54. (Year: 2013).*

(Continued)

*Primary Examiner* — Christopher L Chin
*Assistant Examiner* — Ellis Follett Lusi
(74) *Attorney, Agent, or Firm* — Banner & Witcoff, Ltd.

(57) ABSTRACT

Using protein structural probes one can identify tumor-induced or -produced (TIPS) factors that bind to therapeutic antibodies and change their dynamic structure, thereby negatively affecting their humoral immune functions as well as their pharmacologic activity. Using such protein structural probes and TIPS factors one can screen and identify inhibitors that can counter the binding of TIPS factors to affected therapeutic antibodies. These inhibitors can be used in the presence of a TIPS factor-susceptible antibody (TSA) for treating cancer. An inhibitor can be used alone or in combination with chemotherapy for treating cancer. Patients (Continued)

Figure 1:
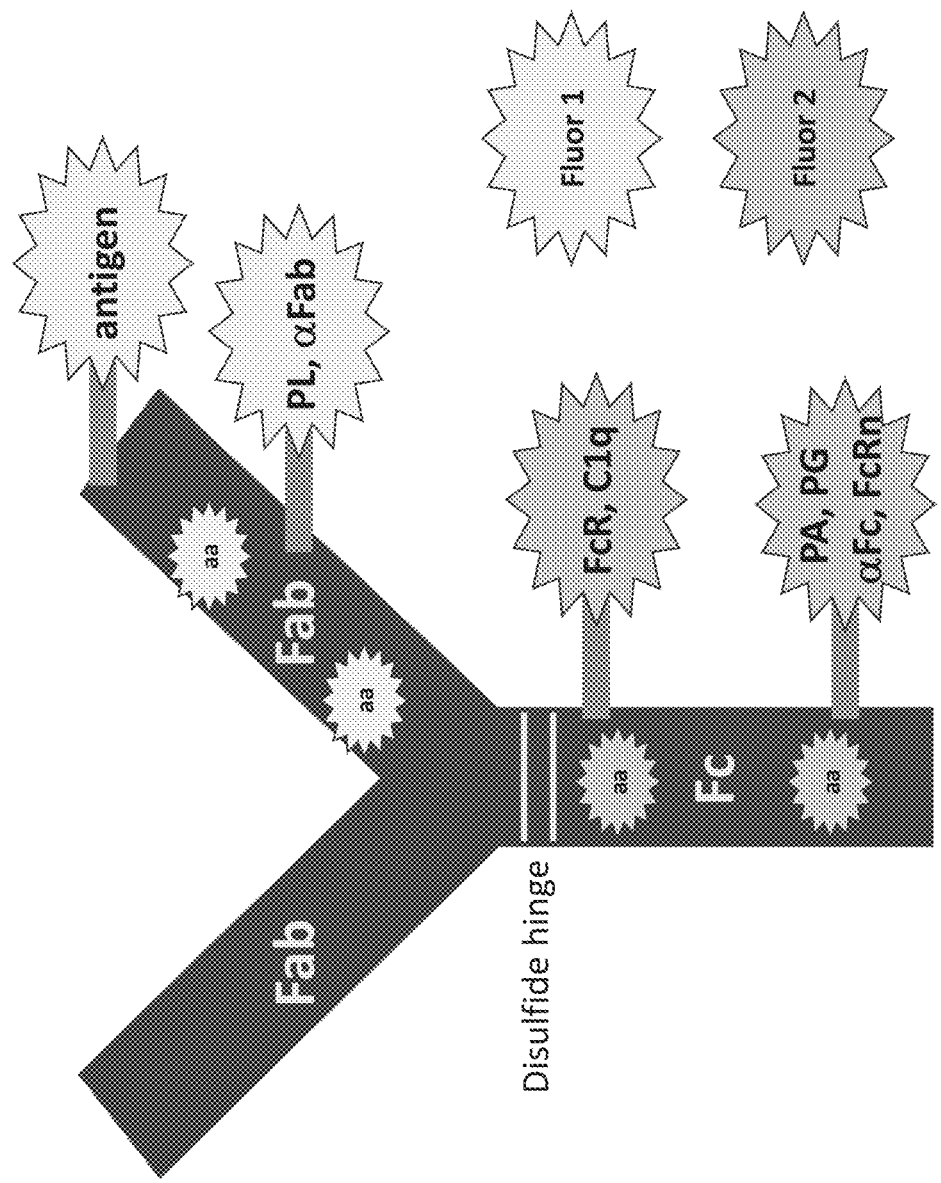

can be screened to identify those with low or no TIPS factor production as candidates for antibody therapy even in the case in which the antibody is a TSA. Conversely, those with high TIPS factor production are candidates for inhibitor therapy.

2 Claims, 6 Drawing Sheets

Specification includes a Sequence Listing.

(51) Int. Cl.
*C07K 16/28* (2006.01)
*C07K 16/32* (2006.01)
*G01N 33/542* (2006.01)

(52) U.S. Cl.
CPC .......... *C07K 16/32* (2013.01); *G01N 33/542* (2013.01); *G01N 2500/02* (2013.01); *G01N 2500/20* (2013.01)

(58) Field of Classification Search
CPC ......... G01N 2021/6441; G01N 33/574; G01N 33/57484; C07K 16/00; C07K 16/2887; C07K 16/32; C07K 2318/00; C07K 16/4208; C07K 16/4283
USPC .................... 435/7.1, 7.9, 7.8; 436/501, 518
See application file for complete search history.

(56) References Cited

U.S. PATENT DOCUMENTS

| | | | |
|---|---|---|---|
| 2010/0190266 | A1 | 7/2010 | Sakita et al. |
| 2011/0071045 | A1 | 3/2011 | Patterson |

FOREIGN PATENT DOCUMENTS

| | | | |
|---|---|---|---|
| WO | 2006074216 | A2 | 7/2006 |
| WO | 2008020823 | A2 | 2/2008 |
| WO | 2015128548 | A1 | 9/2015 |
| WO | 2016104549 | A1 | 6/2016 |
| WO | 2016183387 | A1 | 11/2016 |
| WO | 2017/055399 | A1 | 4/2017 |

OTHER PUBLICATIONS

Goel et al. "Plasticity within the Antigen Combining Site May Manifest as Molecular Mimicry in the Humoral Immune Response," The Journal of Immunology (2004), 173(12):7358-7367 (Year: 2004).*
Lloyd et al. "Modelling the human immune response: performance of a 1011 human antibody repertoire against a broad panel of therapeutically relevant antigens," Protein Engineering, Design & Selection (2009), 22(3):159-168 (Year: 2009).*
Edwards et al. "The remarkable flexibility of the human antibody repertoire; isolation of over one thousand different antibodies to a single protein, BlyS," Journal of Molecular Biology (2003), 334:103-118 (Year: 2003).*
Harlow, E. and Lane, D., Antibodies: A Laboratory Manual (1988) Cold Spring Harbor Laboratory Press, Cold Spring Harbor, NY, pp. 23-26 (Year: 1988).*
Lederman et al. "A single amino acid substitution in a common African allele of the CD4 molecule ablates binding of the monoclonal antibody OKT4" Mol Immunol. Nov. 1991; 28(11):1171-81 (Year: 1991).*
Colman et al. Research in Immunology, 1994; 145(1):33-36) teach that amino acid changes in an antigen can effectively abolish antibody antigen binding entirely (p. 33-34). (Year: 1994).*
Zhang YF, Phung Y, Gao W, Kawa S, Hassan R, Pastan I, Ho M. New high affinity monoclonal antibodies recognize non-overlapping epitopes on mesothelin for monitoring and treating mesothelioma. Sci Rep. May 21, 2015;5:9928. (Year: 2015).*
Manshouri et al. Circulating CD20 is detectable in the plasma of patients with chronic lymphocytic leukemia and is of prognostic significance. Blood 2003; 101 (7): 2507-2513. (Year: 2003).*
Gupta, D., Lis, C.G. Role of CA125 in predicting ovarian cancer survival—a review of the epidemiological literature. J Ovarian Res 2 , 13 (2009) (Year: 2009).*
Jun. 2, 2022—(JP) Notice of Reasons for Rejections—Appl No. 2021-543111.
Jan. 3, 2020—(WO) International Search Report & Written Opinion—App. No. PCT/US2019/051706.
Ko et al., "A novel FRET-based optical fiber biosensor for rapid detection of *Salmonella typhimurium*," Biosensors and Bioelectronics, vol. 21, pp. 1283-1290 (2006).
Li et al., "Fluorescent labels in biosensors for pathogen detection," Crit. Rev. Biotechnol., vol. 35, No. 1, pp. 82-93 (2015).
Saraheimo et al., "Time-Resolved FRET-Based Approach for Antibody Detection—A New Serodiagnostic Concept," PLoS ONE, vol. 8, No. 5, e62739, pp. 1-11 (2013).
Aug. 23, 2023—(EP) Office Action—Appl No. 19865808.0.
May 20, 2022—(EP) Partial supplementary European search report—Appl No. 19865808.0.
Yoshikoshi et al. "Double-Fluorescent-Labeled Single-Chain Antibodies Showing Antigen-Dependent Fluorescense Ratio Change" Bulletin of the Chemical Society of Japan, vol. 89, No. 5, May 15, 2016, pp. 573-580.
Obaid et al. "Activatable clinical fluorophore-quencher antibody pairs as dual molecular probes for the enhanced specificity of image guided surgery" Journal of Biomedical Optics, vol. 22, No. 12, Aug. 29, 2017.
Ko et al. "Development of a novel FRET method for detection of Listeria or Salmonella" Sensors and Actuators B, vol. 96, No. 1-2, Nov. 15, 2003, pp. 372-378.
Smiley et al. "Single-molecule measurements of the opening and closing of the DNA gate by eukaryotic topoisomerase II" PNAS, Mar. 20, 2007, pp. 4840-4845.
Gaborit et al. "Time-resulved Fluorescence Resonance Energy Transfer (TR-FRET) to Analyze the Disruption of EGFR/HER2 Dimers: A New Method to Evaluate the Efficiency of Targeted Therapy Using Monoclonal Antibodies" Journal of Biological Chemistry, vol. 286, No. 13, Apr. 1, 2011, pp. 11337-11345.
Chakraborty et al. "FRET Based Quantification and Screening Technology Platform for the Interactions of Leukocyte Function-Associated Antigen-1 (LFA-1) with InterCellular Adhesion Molecule-1 (ICAM-1)" PLOS ONE, vol. 9, No. 7, Jul. 17, 2014, p. e102572.
Zhang et al. "New High Affinity Monoclonal Antibodies Recognize Non-Overlapping Epitopes On Mesothelin For Monitoring And Treating Mesothelioma" Scientific Reports, vol. 5, May 21, 2015, pp. 1-14.

* cited by examiner

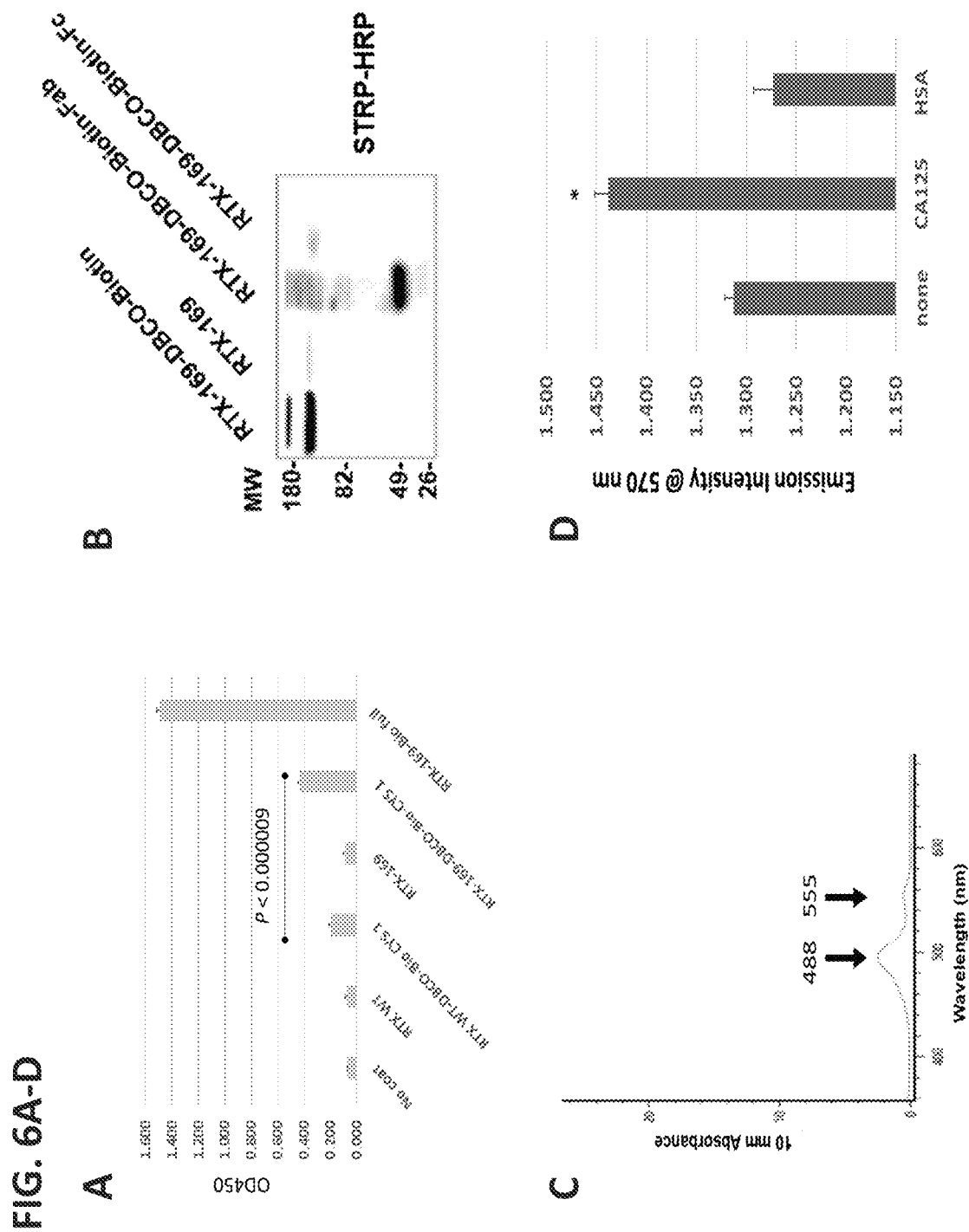
FIG. 6A-D

SEQUENCE LISTING

```
<160> NUMBER OF SEQ ID NOS: 31

<210> SEQ ID NO 1
<211> LENGTH: 992
<212> TYPE: PRT
<213> ORGANISM: Homo Sapiens

<400> SEQUENCE: 1

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
            20                  25                  30

Asp Asn Asn Leu Ser Met Asp Glu Ile Ser Asp Ala Tyr Phe Asp Tyr
        35                  40                  45

His Gly Asp Val Ser Asp Ser Val Asp Pro Val Glu Glu Glu Ile Asp
    50                  55                  60

Glu Ala Leu Ala Lys Ala Leu Ala Glu Ala Lys Glu Thr Ala Lys Lys
65                  70                  75                  80

His Ile Asp Ser Leu Asn His Leu Ser Glu Thr Ala Lys Lys Leu Ala
```

```
                        85                  90                  95
Lys Asn Asp Ile Asp Ser Ala Thr Thr Ile Asn Ala Ile Asn Asp Ile
                100                 105                 110
Val Ala Arg Ala Asp Val Met Glu Arg Lys Thr Ala Glu Lys Glu Glu
                115                 120                 125
Ala Glu Lys Leu Ala Ala Ala Lys Glu Thr Ala Lys Lys His Ile Asp
                130                 135                 140
Glu Leu Lys His Leu Ala Asp Lys Thr Lys Glu Leu Ala Lys Arg Asp
145                 150                 155                 160
Ile Asp Ser Ala Thr Thr Ile Asn Ala Ile Asn Asp Ile Val Ala Arg
                165                 170                 175
Ala Asp Val Met Glu Arg Lys Thr Ala Glu Lys Glu Glu Ala Glu Lys
                180                 185                 190
Leu Ala Ala Ala Lys Glu Thr Ala Lys Lys His Ile Asp Glu Leu Lys
                195                 200                 205
His Leu Ala Asp Lys Thr Lys Glu Leu Ala Lys Arg Asp Ile Asp Ser
                210                 215                 220
Ala Thr Thr Ile Asp Ala Ile Asn Asp Ile Val Ala Arg Ala Asp Val
225                 230                 235                 240
Met Glu Arg Lys Leu Ser Glu Lys Glu Thr Pro Glu Pro Glu Glu Glu
                245                 250                 255
Val Thr Ile Lys Ala Asn Leu Ile Phe Ala Asp Gly Ser Thr Gln Asn
                260                 265                 270
Ala Glu Phe Lys Gly Thr Phe Ala Lys Ala Val Ser Asp Ala Tyr Ala
                275                 280                 285
Tyr Ala Asp Ala Leu Lys Lys Asp Asn Gly Glu Tyr Thr Val Asp Val
                290                 295                 300
Ala Asp Lys Gly Leu Thr Leu Asn Ile Lys Phe Ala Gly Lys Lys Glu
305                 310                 315                 320
Lys Pro Glu Glu Pro Lys Glu Glu Val Thr Ile Lys Val Asn Leu Ile
                325                 330                 335
Phe Ala Asp Gly Lys Thr Gln Thr Ala Glu Phe Lys Gly Thr Phe Glu
                340                 345                 350
Glu Ala Thr Ala Lys Ala Tyr Ala Tyr Ala Asp Leu Leu Ala Lys Glu
                355                 360                 365
Asn Gly Glu Tyr Thr Ala Asp Leu Glu Asp Gly Gly Asn Thr Ile Asn
                370                 375                 380
Ile Lys Phe Ala Gly Lys Glu Thr Pro Glu Thr Pro Glu Glu Pro Lys
385                 390                 395                 400
Glu Glu Val Thr Ile Lys Val Asn Leu Ile Phe Ala Asp Gly Lys Ile
                405                 410                 415
Gln Thr Ala Glu Phe Lys Gly Thr Phe Glu Glu Ala Thr Ala Lys Ala
                420                 425                 430
Tyr Ala Tyr Ala Asn Leu Leu Ala Lys Glu Asn Gly Glu Tyr Thr Ala
                435                 440                 445
Asp Leu Glu Asp Gly Gly Asn Thr Ile Asn Ile Lys Phe Ala Gly Lys
                450                 455                 460
Glu Thr Pro Glu Thr Pro Glu Glu Pro Lys Glu Glu Val Thr Ile Lys
465                 470                 475                 480
Val Asn Leu Ile Phe Ala Asp Gly Lys Thr Gln Thr Ala Glu Phe Lys
                485                 490                 495
Gly Thr Phe Glu Glu Ala Thr Ala Glu Ala Tyr Arg Tyr Ala Asp Leu
                500                 505                 510
```

```
Leu Ala Lys Val Asn Gly Glu Tyr Thr Ala Asp Leu Glu Asp Gly Gly
        515                 520                 525

Tyr Thr Ile Asn Ile Lys Phe Ala Gly Lys Glu Gln Pro Gly Glu Asn
        530                 535                 540

Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
                580                 585                 590

Asn Glu Ile Leu Lys Ala His Ala Gly Glu Thr Pro Glu Leu Lys
        595                 600                 605

Asp Gly Tyr Ala Thr Tyr Glu Glu Ala Glu Ala Ala Lys Glu Ala
        610                 615                 620

Leu Lys Asn Asp Asp Val Asn Asn Ala Tyr Glu Ile Val Gln Gly Ala
625                 630                 635                 640

Asp Gly Arg Tyr Tyr Tyr Val Leu Lys Ile Glu Val Ala Asp Glu Glu
                645                 650                 655

Glu Pro Gly Glu Asp Thr Pro Glu Val Gln Gly Tyr Ala Thr Tyr
                660                 665                 670

Glu Glu Ala Glu Ala Ala Lys Glu Ala Leu Lys Glu Asp Lys Val
                675                 680                 685

Asn Asn Ala Tyr Glu Val Val Gln Gly Ala Asp Gly Arg Tyr Tyr Tyr
        690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Lys Asn Ala
                725                 730                 735

Lys Glu Asp Ala Ile Lys Glu Leu Lys Glu Ala Gly Ile Ser Ser Asp
                740                 745                 750

Ile Tyr Phe Asp Ala Ile Asn Lys Ala Lys Thr Val Glu Gly Val Glu
        755                 760                 765

Ala Leu Lys Asn Glu Ile Leu Lys Ala His Ala Glu Lys Pro Gly Glu
        770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
                805                 810                 815

Phe Asn Leu Ile Asn Lys Ala Lys Thr Val Glu Gly Val Glu Ser Leu
                820                 825                 830

Lys Asn Glu Ile Leu Lys Ala His Ala Glu Lys Pro Gly Glu Asn Pro
        835                 840                 845

Gly Ile Thr Ile Asp Glu Trp Leu Leu Lys Asn Ala Lys Glu Asp Ala
        850                 855                 860

Ile Lys Glu Leu Lys Glu Ala Gly Ile Thr Ser Asp Ile Tyr Phe Asp
865                 870                 875                 880

Ala Ile Asn Lys Ala Lys Thr Ile Glu Gly Val Glu Ala Leu Lys Asn
                885                 890                 895

Glu Ile Leu Lys Ala His Lys Lys Asp Glu Glu Pro Gly Lys Lys Pro
                900                 905                 910

Gly Glu Asp Lys Lys Pro Glu Asp Lys Pro Gly Glu Asp Lys Lys
        915                 920                 925
```

```
Pro Glu Asp Lys Lys Pro Gly Glu Asp Lys Lys Pro Glu Asp Lys Lys
            930                 935                 940

Pro Gly Lys Thr Asp Lys Asp Ser Pro Asn Lys Lys Lys Ala Lys
945                 950                 955                 960

Leu Pro Lys Ala Gly Ser Glu Ala Glu Ile Leu Thr Leu Ala Ala Ala
                965                 970                 975

Ala Leu Ser Thr Ala Ala Gly Ala Tyr Val Ser Leu Lys Lys Arg Lys
            980                 985                 990

<210> SEQ ID NO 2
<211> LENGTH: 508
<212> TYPE: PRT
<213> ORGANISM: Homo Sapiens

<400> SEQUENCE: 2

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Lys Phe Asn Lys Asp Gln Gln Ser Ala Phe Tyr Glu Ile Leu
            100                 105                 110

Asn Met Pro Asn Leu Asn Glu Glu Gln Arg Asn Gly Phe Ile Gln Ser
        115                 120                 125

Leu Lys Asp Asp Pro Ser Gln Ser Thr Asn Val Leu Gly Glu Ala Lys
130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320
```

```
Asn Asp Ala Gln Ala Pro Lys Glu Glu Asp Asn Asn Lys Pro Gly Lys
                325                 330                 335

Glu Asp Gly Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
        355                 360                 365

Glu Asp Asn Lys Lys Pro Gly Lys Glu Asp Gly Asn Lys Pro Gly Lys
    370                 375                 380

Glu Asp Gly Asn Lys Pro Gly Lys Glu Asp Gly Asn Lys Pro Gly Lys
385                 390                 395                 400

Glu Asp Gly Asn Lys Pro Gly Lys Glu Asp Gly Asn Gly Val His Val
                405                 410                 415

Val Lys Pro Gly Asp Thr Val Asn Asp Ile Ala Lys Ala Asn Gly Thr
            420                 425                 430

Thr Ala Asp Lys Ile Ala Ala Asp Asn Lys Leu Ala Asp Lys Asn Met
        435                 440                 445

Ile Lys Pro Gly Gln Glu Leu Val Val Asp Lys Lys Gln Pro Ala Asn
    450                 455                 460

His Ala Asp Ala Asn Lys Ala Gln Ala Leu Pro Glu Thr Gly Glu Glu
465                 470                 475                 480

Asn Pro Phe Ile Gly Thr Thr Val Phe Gly Gly Leu Ser Leu Ala Leu
                485                 490                 495

Gly Ala Ala Leu Leu Ala Gly Arg Arg Arg Glu Leu
            500                 505

<210> SEQ ID NO 3
<211> LENGTH: 593
<212> TYPE: PRT
<213> ORGANISM: Homo Sapiens

<400> SEQUENCE: 3

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
        115                 120                 125

Asn Asn Ala Lys Thr Val Glu Gly Val Lys Asp Leu Gln Ala Gln Val
    130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
```

-continued

```
                180                 185                 190
Tyr Gly Val Ser Asp Tyr His Lys Asn Leu Ile Asn Asn Ala Lys Thr
                195                 200                 205
Val Glu Gly Val Lys Asp Leu Gln Ala Gln Val Val Glu Ser Ala Lys
                210                 215                 220
Lys Ala Arg Ile Ser Glu Ala Thr Asp Gly Leu Ser Asp Phe Leu Lys
225                 230                 235                 240
Ser Gln Thr Pro Ala Glu Asp Thr Val Lys Ser Ile Glu Leu Ala Glu
                245                 250                 255
Ala Lys Val Leu Ala Asn Arg Glu Leu Asp Lys Tyr Gly Val Ser Asp
                260                 265                 270
Tyr Tyr Lys Asn Leu Ile Asn Asn Ala Lys Thr Val Glu Gly Val Lys
                275                 280                 285
Ala Leu Ile Asp Glu Ile Leu Ala Ala Leu Pro Lys Thr Asp Thr Tyr
                290                 295                 300
Lys Leu Ile Leu Asn Gly Lys Thr Leu Lys Gly Glu Thr Thr Thr Glu
305                 310                 315                 320
Ala Val Asp Ala Ala Thr Ala Glu Lys Val Phe Lys Gln Tyr Ala Asn
                325                 330                 335
Asp Asn Gly Val Asp Gly Glu Trp Thr Tyr Asp Asp Ala Thr Lys Thr
                340                 345                 350
Phe Thr Val Thr Glu Lys Pro Glu Val Ile Asp Ala Ser Glu Leu Thr
                355                 360                 365
Pro Ala Val Thr Thr Tyr Lys Leu Val Ile Asn Gly Lys Thr Leu Lys
                370                 375                 380
Gly Glu Thr Thr Thr Glu Ala Val Asp Ala Ala Thr Ala Glu Lys Val
385                 390                 395                 400
Phe Lys Gln Tyr Ala Asn Asp Asn Gly Val Asp Gly Glu Trp Thr Tyr
                405                 410                 415
Asp Asp Ala Thr Lys Thr Phe Thr Val Thr Glu Lys Pro Glu Val Ile
                420                 425                 430
Asp Ala Ser Glu Leu Thr Pro Ala Val Thr Thr Tyr Lys Leu Val Ile
                435                 440                 445
Asn Gly Lys Thr Leu Lys Gly Glu Thr Thr Thr Lys Ala Val Asp Ala
                450                 455                 460
Glu Thr Ala Glu Lys Ala Phe Lys Gln Tyr Ala Asn Asp Asn Gly Val
465                 470                 475                 480
Asp Gly Val Trp Thr Tyr Asp Asp Ala Thr Lys Thr Phe Thr Val Thr
                485                 490                 495
Glu Met Val Thr Glu Val Pro Gly Asp Ala Pro Thr Glu Pro Glu Lys
                500                 505                 510
Pro Glu Ala Ser Ile Pro Leu Val Pro Leu Thr Pro Ala Thr Pro Ile
                515                 520                 525
Ala Lys Asp Asp Ala Lys Lys Asp Asp Thr Lys Lys Glu Asp Ala Lys
                530                 535                 540
Lys Pro Glu Ala Lys Lys Glu Asp Ala Lys Lys Ala Glu Thr Leu Pro
545                 550                 555                 560
Thr Thr Gly Glu Gly Ser Asn Pro Phe Phe Thr Ala Ala Ala Leu Ala
                565                 570                 575
Val Met Ala Gly Ala Gly Ala Leu Ala Val Ala Ser Lys Arg Lys Glu
                580                 585                 590
Asp
```

<210> SEQ ID NO 4
<211> LENGTH: 374
<212> TYPE: PRT
<213> ORGANISM: Homo Sapiens

<400> SEQUENCE: 4

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
    275                 280                 285

Val Trp Phe His Val Leu Phe Tyr Leu Ala Val Gly Ile Met Phe Leu
            290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
    370

<210> SEQ ID NO 5
<211> LENGTH: 317
<212> TYPE: PRT
<213> ORGANISM: Homo Sapiens

<400> SEQUENCE: 5

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn Asn
305                 310                 315

<210> SEQ ID NO 6
<211> LENGTH: 310
<212> TYPE: PRT
<213> ORGANISM: Homo Sapiens

<400> SEQUENCE: 6

Met Gly Ile Leu Ser Phe Leu Pro Val Leu Ala Thr Glu Ser Asp Trp
1               5                   10                  15

```
Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
                35                  40                  45

Lys Ala Val Leu Lys Leu Glu Pro Gln Trp Ile Asn Val Leu Gln Glu
 50                  55                  60

Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
        210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300

Asp Asp Gln Asn Arg Ile
305                 310

<210> SEQ ID NO 7
<211> LENGTH: 323
<212> TYPE: PRT
<213> ORGANISM: Homo Sapiens

<400> SEQUENCE: 7

Met Gly Ile Leu Ser Phe Leu Pro Val Leu Ala Thr Glu Ser Asp Trp
 1               5                  10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
                35                  40                  45

Lys Ala Val Leu Lys Leu Glu Pro Gln Trp Ile Asn Val Leu Gln Glu
 50                  55                  60

Asp Ser Val Thr Leu Thr Cys Arg Gly Thr His Ser Pro Glu Ser Asp
```

```
                65                  70                  75                  80
Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
                100                 105                 110

Cys Gln Thr Gly Gln Thr Ser Leu Ser Asp Pro Val His Leu Thr Val
                115                 120                 125

Leu Ser Glu Trp Leu Val Leu Gln Thr Pro His Leu Glu Phe Gln Glu
            130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
                180                 185                 190

Asp Tyr His Cys Thr Gly Asn Ile Gly Tyr Thr Leu Tyr Ser Ser Lys
                195                 200                 205

Pro Val Thr Ile Thr Val Gln Ala Pro Ser Ser Ser Pro Met Gly Ile
            210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Ser
                245                 250                 255

Thr Asp Pro Val Lys Ala Ala Gln Phe Glu Pro Pro Gly Arg Gln Met
                260                 265                 270

Ile Ala Ile Arg Lys Arg Gln Pro Glu Glu Thr Asn Asn Asp Tyr Glu
                275                 280                 285

Thr Ala Asp Gly Gly Tyr Met Thr Leu Asn Pro Arg Ala Pro Thr Asp
            290                 295                 300

Asp Asp Lys Asn Ile Tyr Leu Thr Leu Pro Pro Asn Asp His Val Asn
305                 310                 315                 320

Ser Asn Asn

<210> SEQ ID NO 8
<211> LENGTH: 254
<212> TYPE: PRT
<213> ORGANISM: Homo Sapiens

<400> SEQUENCE: 8

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
            50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
```

115                 120                 125
His Ser Trp Lys Asn Thr Ala Leu His Lys Val Thr Tyr Leu Gln Asn
    130                 135                 140
Gly Lys Gly Arg Lys Tyr Phe His His Asn Ser Asp Phe Tyr Ile Pro
145                 150                 155                 160
Lys Ala Thr Leu Lys Asp Ser Gly Ser Tyr Phe Cys Arg Gly Leu Phe
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Phe Pro Pro Gly Tyr Gln
            195                 200                 205
Val Ser Phe Cys Leu Val Met Val Leu Leu Phe Ala Val Asp Thr Gly
        210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250

<210> SEQ ID NO 9
<211> LENGTH: 233
<212> TYPE: PRT
<213> ORGANISM: Homo Sapiens

<400> SEQUENCE: 9

Met Trp Gln Leu Leu Leu Pro Thr Ala Leu Leu Leu Val Ser Ala
1               5                   10                  15
Gly Met Arg Thr Glu Asp Leu Pro Lys Ala Val Val Phe Leu Glu Pro
            20                  25                  30
Gln Trp Tyr Ser Val Leu Glu Lys Asp Ser Val Thr Leu Lys Cys Gln
        35                  40                  45
Gly Ala Tyr Ser Pro Glu Asp Asn Ser Thr Gln Trp Phe His Asn Glu
    50                  55                  60
Ser Leu Ile Ser Ser Gln Ala Ser Ser Tyr Phe Ile Asp Ala Ala Thr
65                  70                  75                  80
Val Asn Asp Ser Gly Glu Tyr Arg Cys Gln Thr Asn Leu Ser Thr Leu
                85                  90                  95
Ser Asp Pro Val Gln Leu Glu Val His Ile Gly Trp Leu Leu Leu Gln
            100                 105                 110
Ala Pro Arg Trp Val Phe Lys Glu Glu Asp Pro Ile His Leu Arg Cys
        115                 120                 125
His Ser Trp Lys Asn Thr Ala Leu His Lys Val Thr Tyr Leu Gln Asn
    130                 135                 140
Gly Lys Asp Arg Lys Tyr Phe His His Asn Ser Asp Phe His Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Ser Pro Pro Gly Tyr Gln
            195                 200                 205
Val Ser Phe Cys Leu Val Met Val Leu Leu Phe Ala Val Asp Thr Gly
        210                 215                 220
Leu Tyr Phe Ser Val Lys Thr Asn Ile
225                 230

<210> SEQ ID NO 10
<211> LENGTH: 365
<212> TYPE: PRT
<213> ORGANISM: Homo Sapiens

<400> SEQUENCE: 10

```
Met Gly Val Pro Arg Pro Gln Pro Trp Ala Leu Gly Leu Leu Leu Phe
1               5                  10                 15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365
```

<210> SEQ ID NO 11

<211> LENGTH: 977
<212> TYPE: PRT
<213> ORGANISM: Homo Sapiens

<400> SEQUENCE: 11

```
Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205

Leu Thr Cys Glu Thr Gln Leu Ser Leu Glu Arg Ser Asp Val Pro Leu
    210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro Tyr Ser Val Ile Ser Asp
            260                 265                 270

Ser Pro Arg Ser Trp Ile Gln Val Gln Ile Pro Ala Ser His Pro Val
        275                 280                 285

Leu Thr Leu Ser Pro Glu Lys Ala Leu Asn Phe Glu Gly Thr Lys Val
    290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
        355                 360                 365

Val Ser Leu Ser Val Thr Val Pro Val Ser His Pro Val Leu Asn Leu
    370                 375                 380

Ser Ser Pro Glu Asp Leu Ile Phe Glu Gly Ala Lys Val Thr Leu His
```

-continued

```
            385                 390                 395                 400
        Cys Glu Ala Gln Arg Gly Ser Leu Pro Ile Leu Tyr Gln Phe His His
                        405                 410                 415

Glu Gly Ala Ala Leu Glu Arg Arg Ser Ala Asn Ser Ala Gly Gly Val
                        420                 425                 430

Ala Ile Ser Phe Ser Leu Thr Ala Glu His Ser Gly Asn Tyr Tyr Cys
                        435                 440                 445

Thr Ala Asp Asn Gly Phe Gly Pro Gln Arg Ser Lys Ala Val Ser Leu
                        450                 455                 460

Ser Val Thr Val Pro Val Ser His Pro Val Leu Thr Leu Ser Ser Ala
        465                 470                 475                 480

Glu Ala Leu Thr Phe Glu Gly Ala Thr Val Thr Leu His Cys Glu Val
                        485                 490                 495

Gln Arg Gly Ser Pro Gln Ile Leu Tyr Gln Phe Tyr His Glu Asp Met
                        500                 505                 510

Pro Leu Trp Ser Ser Ser Thr Pro Ser Val Gly Arg Val Ser Phe Ser
                        515                 520                 525

Phe Ser Leu Thr Glu Gly His Ser Gly Asn Tyr Tyr Cys Thr Ala Asp
                        530                 535                 540

Asn Gly Phe Gly Pro Gln Arg Ser Glu Val Val Ser Leu Phe Val Thr
        545                 550                 555                 560

Val Pro Val Ser Arg Pro Ile Leu Thr Leu Arg Val Pro Arg Ala Gln
                        565                 570                 575

Ala Val Val Gly Asp Leu Leu Glu Leu His Cys Glu Ala Pro Arg Gly
                        580                 585                 590

Ser Pro Pro Ile Leu Tyr Trp Phe Tyr His Glu Asp Val Thr Leu Gly
                        595                 600                 605

Ser Ser Ser Ala Pro Ser Gly Gly Glu Ala Ser Phe Asn Leu Ser Leu
                        610                 615                 620

Thr Ala Glu His Ser Gly Asn Tyr Ser Cys Glu Ala Asn Asn Gly Leu
        625                 630                 635                 640

Val Ala Gln His Ser Asp Thr Ile Ser Leu Ser Val Ile Val Pro Val
                        645                 650                 655

Ser Arg Pro Ile Leu Thr Phe Arg Ala Pro Arg Ala Gln Ala Val Val
                        660                 665                 670

Gly Asp Leu Leu Glu Leu His Cys Glu Ala Leu Arg Gly Ser Ser Pro
                        675                 680                 685

Ile Leu Tyr Trp Phe Tyr His Glu Asp Val Thr Leu Gly Lys Ile Ser
                        690                 695                 700

Ala Pro Ser Gly Gly Gly Ala Ser Phe Asn Leu Ser Leu Thr Thr Glu
        705                 710                 715                 720

His Ser Gly Ile Tyr Ser Cys Glu Ala Asp Asn Gly Leu Glu Ala Gln
                        725                 730                 735

Arg Ser Glu Met Val Thr Leu Lys Val Ala Val Pro Val Ser Arg Pro
                        740                 745                 750

Val Leu Thr Leu Arg Ala Pro Gly Thr His Ala Ala Val Gly Asp Leu
                        755                 760                 765

Leu Glu Leu His Cys Glu Ala Leu Arg Gly Ser Pro Leu Ile Leu Tyr
                        770                 775                 780

Arg Phe Phe His Glu Asp Val Thr Leu Gly Asn Arg Ser Ser Pro Ser
        785                 790                 795                 800

Gly Gly Ala Ser Leu Asn Leu Ser Leu Thr Ala Glu His Ser Gly Asn
                        805                 810                 815
```

Tyr Ser Cys Glu Ala Asp Asn Gly Leu Gly Ala Gln Arg Ser Glu Thr
                820                 825                 830

Val Thr Leu Tyr Ile Thr Gly Leu Thr Ala Asn Arg Ser Gly Pro Phe
            835                 840                 845

Ala Thr Gly Val Ala Gly Gly Leu Leu Ser Ile Ala Gly Leu Ala Ala
850                 855                 860

Gly Ala Leu Leu Leu Tyr Cys Trp Leu Ser Arg Lys Ala Gly Arg Lys
865                 870                 875                 880

Pro Ala Ser Asp Pro Ala Arg Ser Pro Ser Asp Ser Asp Ser Gln Glu
                885                 890                 895

Pro Thr Tyr His Asn Val Pro Ala Trp Glu Glu Leu Gln Pro Val Tyr
            900                 905                 910

Thr Asn Ala Asn Pro Arg Gly Glu Asn Val Val Tyr Ser Glu Val Arg
        915                 920                 925

Ile Ile Gln Glu Lys Lys Lys His Ala Val Ala Ser Asp Pro Arg His
    930                 935                 940

Leu Arg Asn Lys Gly Ser Pro Ile Ile Tyr Ser Glu Val Lys Val Ala
945                 950                 955                 960

Ser Thr Pro Val Ser Gly Ser Leu Phe Leu Ala Ser Ser Ala Pro His
                965                 970                 975

Arg

<210> SEQ ID NO 12
<211> LENGTH: 249
<212> TYPE: PRT
<213> ORGANISM: Mus musculus

<400> SEQUENCE: 12

Met Trp Gln Leu Leu Leu Pro Thr Ala Leu Val Leu Thr Ala Phe Ser
1               5                   10                  15

Gly Ile Gln Ala Gly Leu Gln Lys Ala Val Val Asn Leu Asp Pro Lys
            20                  25                  30

Trp Val Arg Val Leu Glu Glu Asp Ser Val Thr Leu Arg Cys Gln Gly
        35                  40                  45

Thr Phe Ser Pro Glu Asp Asn Ser Ile Lys Trp Phe His Asn Glu Ser
    50                  55                  60

Leu Ile Pro His Gln Asp Ala Asn Tyr Val Ile Gln Ser Ala Arg Val
65                  70                  75                  80

Lys Asp Ser Gly Met Tyr Arg Cys Gln Thr Ala Leu Ser Thr Ile Ser
                85                  90                  95

Asp Pro Val Gln Leu Glu Val His Met Gly Trp Leu Leu Leu Gln Thr
            100                 105                 110

Thr Lys Trp Leu Phe Gln Glu Gly Asp Pro Ile His Leu Arg Cys His
        115                 120                 125

Ser Trp Gln Asn Arg Pro Val Arg Lys Val Thr Tyr Leu Gln Asn Gly
    130                 135                 140

Lys Gly Lys Lys Tyr Phe His Glu Asn Ser Glu Leu Leu Ile Pro Lys
145                 150                 155                 160

Ala Thr His Asn Asp Ser Gly Ser Tyr Phe Cys Arg Gly Leu Ile Gly
                165                 170                 175

His Asn Asn Lys Ser Ser Ala Ser Phe Arg Ile Ser Leu Gly Asp Pro
            180                 185                 190

Gly Ser Pro Ser Met Phe Pro Pro Trp His Gln Ile Thr Phe Cys Leu
        195                 200                 205

```
Leu Ile Gly Leu Leu Phe Ala Ile Asp Thr Val Leu Tyr Phe Ser Val
            210                 215                 220

Arg Arg Gly Leu Gln Ser Pro Val Ala Asp Tyr Glu Glu Pro Lys Ile
225                 230                 235                 240

Gln Trp Ser Lys Glu Pro Gln Asp Lys
                245

<210> SEQ ID NO 13
<211> LENGTH: 245
<212> TYPE: PRT
<213> ORGANISM: Homo Sapiens

<400> SEQUENCE: 13

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 14
<211> LENGTH: 11
<212> TYPE: PRT
<213> ORGANISM: Homo Sapiens

<400> SEQUENCE: 14

Gly Phe Asp Leu Gly Phe Tyr Phe Tyr Ala Cys
1               5                   10

<210> SEQ ID NO 15
```

```
<211> LENGTH: 18
<212> TYPE: PRT
<213> ORGANISM: Homo Sapiens

<400> SEQUENCE: 15

Cys Ile Tyr Thr Ala Gly Ser Gly Ser Thr Tyr Tyr Ala Ser Trp Ala
1               5                   10                  15
Lys Gly

<210> SEQ ID NO 16
<211> LENGTH: 15
<212> TYPE: PRT
<213> ORGANISM: Homo Sapiens

<400> SEQUENCE: 16

Ala Arg Ser Thr Ala Asn Thr Arg Ser Thr Tyr Tyr Leu Asn Leu
1               5                   10                  15

<210> SEQ ID NO 17
<211> LENGTH: 11
<212> TYPE: PRT
<213> ORGANISM: Homo Sapiens

<400> SEQUENCE: 17

Gln Ala Ser Gln Arg Ile Ser Ser Tyr Leu Ser
1               5                   10

<210> SEQ ID NO 18
<211> LENGTH: 7
<212> TYPE: PRT
<213> ORGANISM: Homo Sapiens

<400> SEQUENCE: 18

Gly Ala Ser Thr Leu Ala Ser
1               5

<210> SEQ ID NO 19
<211> LENGTH: 13
<212> TYPE: PRT
<213> ORGANISM: Homo Sapiens

<400> SEQUENCE: 19

Gln Ser Tyr Ala Tyr Phe Asp Ser Asn Asn Trp His Ala
1               5                   10

<210> SEQ ID NO 20
<211> LENGTH: 8
<212> TYPE: PRT
<213> ORGANISM: Homo Sapiens

<400> SEQUENCE: 20

Gly Tyr Thr Phe Thr Ser Tyr Asn
1               5

<210> SEQ ID NO 21
<211> LENGTH: 8
<212> TYPE: PRT
<213> ORGANISM: Homo Sapiens

<400> SEQUENCE: 21

Ile Tyr Pro Gly Asn Gly Asp Thr
1               5

<210> SEQ ID NO 22
```

```
<211> LENGTH: 14
<212> TYPE: PRT
<213> ORGANISM: Homo Sapiens

<400> SEQUENCE: 22

Ala Arg Ser Thr Tyr Tyr Gly Gly Asp Trp Tyr Phe Asn Val
1               5                   10

<210> SEQ ID NO 23
<211> LENGTH: 6
<212> TYPE: PRT
<213> ORGANISM: Homo Sapiens

<400> SEQUENCE: 23

Ser Ser Ser Val Ser Tyr
1               5

<210> SEQ ID NO 24
<211> LENGTH: 3
<212> TYPE: PRT
<213> ORGANISM: Homo Sapiens

<400> SEQUENCE: 24

Ala Thr Ser
1

<210> SEQ ID NO 25
<211> LENGTH: 9
<212> TYPE: PRT
<213> ORGANISM: Homo Sapiens

<400> SEQUENCE: 25

Gln Gln Trp Thr Ser Asn Pro Pro Thr
1               5

<210> SEQ ID NO 26
<211> LENGTH: 213
<212> TYPE: PRT
<213> ORGANISM: Artificial Sequence
<220> FEATURE:
<223> OTHER INFORMATION: recombinant chimeric murine/human; wild type
      light chain rituximab

<400> SEQUENCE: 26

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 27
<211> LENGTH: 451
<212> TYPE: PRT
<213> ORGANISM: Artificial Sequence
<220> FEATURE:
<223> OTHER INFORMATION: recombinant chimeric murine/human; wildtype
      heavy chain rituximab

<400> SEQUENCE: 27

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
                        275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 28
<211> LENGTH: 451
<212> TYPE: PRT
<213> ORGANISM: Artificial Sequence
<220> FEATURE:
<223> OTHER INFORMATION: recombinant chimeric murine/human; mutant heavy
      chain rituximab S169C

<400> SEQUENCE: 28

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Cys Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 29
<211> LENGTH: 642
<212> TYPE: DNA
<213> ORGANISM: Artificial Sequence
<220> FEATURE:
<223> OTHER INFORMATION: recombinant chimeric murine/human; wildtype
      light chain rituximab

<400> SEQUENCE: 29
caaattgtcc tgagccagtc tccggcgatt ctcagcgcat ctccagggga aaaggttact      60
atgacgtgta gagcttcatc ctccgtgtca tatattcatt ggtttcagca gaagccaggt    120
tctagtccaa aaccttggat ttacgctacg agcaatttgg catcaggcgt tcctgtacgg    180
tttagcggta gcggcagcgg cacctcatat tccttgacga taagccgggt cgaggcagaa    240
gacgcggcca cctattattg tcagcaatgg actagtaacc cccgacatt tggaggggga    300 actaaacttg aaattaagcg aactgtggct gcaccatctg tcttcatctt cccgccatct    360
gatgagcagt tgaaatctgg aactgcctct gttgtgtgcc tgctgaataa cttctatccc    420
```

```
agagaggcca aagtacagtg aaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642

<210> SEQ ID NO 30
<211> LENGTH: 1356
<212> TYPE: DNA
<213> ORGANISM: Artificial Sequence
<220> FEATURE:
<223> OTHER INFORMATION: recombinant chimeric murine/human; wild type
      heavy chain rituximab

<400> SEQUENCE: 30
caagtgcagc tgcagcagcc gggtgcagaa ctcgtgaagc caggggcctc agtgaagatg      60
tcctgcaaag ccagcggcta caccttcacc tcctacaaca tgcactgggt caagcaaact     120
cctggacgcg gacttgagtg gattggtgct atctaccccg gaaacggcga caccagctac     180
aatcagaagt ttaaggggaa ggccactctg actgccgaca gtcgtcctc gacggcgtac     240 atgcagctga gctcgctgac ctccgaggac tccgccgtgt attactgtgc tcggtccacc     300
tactacggcg gcgattggta cttcaacgtc tggggagccg gaaccactgt gaccgtgtca     360
gccgcatcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356

<210> SEQ ID NO 31
<211> LENGTH: 1356
<212> TYPE: DNA
<213> ORGANISM: Artificial Sequence
<220> FEATURE:
<223> OTHER INFORMATION: recombinant chimeric murine/human; rituximab
      mutant S169C heavy chain

<400> SEQUENCE: 31
caagtgcagc tgcagcagcc gggtgcagaa ctcgtgaagc caggggcctc agtgaagatg      60
tcctgcaaag ccagcggcta caccttcacc tcctacaaca tgcactgggt caagcaaact     120
```

-continued

```
cctggacgcg gacttgagtg gattggtgct atctaccccg gaaacggcga caccagctac        180
aatcagaagt ttaaggggaa ggccactctg actgccgaca agtcgtcctc gacggcgtac        240
atgcagctga gctcgctgac ctccgaggac tccgccgtgt attactgtgc tcggtccacc        300
tactacggcg gcgattggta cttcaacgtc tggggagccg gaaccactgt gaccgtgtca        360
gccgcatcca ccaagggccc atcggtcttc ccctggcac cctcctccaa gagcacctct         420 ggggcacag cggccctggg ctgcctggtc aaggactact tccccgaacc ggtgacggtg         480
tcgtggaact caggcgccct gacctgcggc gtgcacacct cccggctgt cctacagtcc         540 tcaggactct actccctcag cagcgtggtg accgtgccct ccagcagctt gggcacccag        600
acctacatct gcaacgtgaa tcacaagccc agcaacacca aggtggacaa gaaagttgag        660
cccaaatctt gtgacaaaac tcacacatgc ccaccgtgcc cagcacctga actcctgggg        720
ggaccgtcag tcttcctctt ccccccaaaa cccaaggaca ccctcatgat ctcccggacc        780
cctgaggtca catgcgtggt ggtggacgtg agccacgaag accctgaggt caagttcaac        840
tggtacgtgg acggcgtgga ggtgcataat gccaagacaa agccgcggga ggagcagtac        900
aacagcacgt accgtgtggt cagcgtcctc accgtcctgc accaggactg gctgaatggc        960
aaggagtaca agtgcaaggt ctccaacaaa gccctcccag ccccatcga gaaaaccatc        1020 tccaaagcca aagggcagcc ccgagaacca caggtgtaca ccctgccccc atcccgggat       1080
gagctgacca agaaccaggt cagcctgacc tgcctggtca aaggcttcta tcccagcgac       1140
atcgccgtgg agtgggagag caatgggcag ccggagaaca actacaagac cacgcctccc       1200
gtgctggact ccgacggctc cttcttcctc tatagcaagc tcaccgtgga caagagcagg       1260
tggcagcagg ggaacgtctt ctcatgctcc gtgatgcatg aggctctgca caaccactac       1320
acgcagaaga gcctctccct gtctccgggt aaatga                                 1356
```

COMPOSITION AND METHODS FOR MEASURING ANTIBODY DYNAMICS

CROSS-REFERENCE TO RELATED APPLICATIONS

This application is a U.S. National Stage application under 35 U.S.C. § 371 of International Application PCT/US2019/051706, filed Sep. 18, 2019, which claims the benefit of priority to U.S. Provisional Application No. 62/737,414, filed Sep. 27, 2018. This application claims the benefit of the filing date of each of these prior applications. The content of each prior filing is expressly incorporated herein.

TECHNICAL FIELD OF THE INVENTION

This invention is related to the area of humoral immuno-oncology. In particular, it relates to methods, kits, and compositions to improve antibody efficacy in inhibiting cancer growth or treating other diseases.

BACKGROUND OF THE INVENTION

The human immune system is comprised of two major types of adaptive immunity, namely cellular and humoral immunity. With the recent discovery of immune checkpoint inhibitors mediating cellular immunity (Hodi F S, et al. N Engl J Med 363:711-723, 2010), the pursuit of agents that can block these pathways have gained significant knowledge on approaches to overcome this tumor survival mechanism. While several commercially approved therapeutic anti-cancer antibodies have been reported to exhibit their anti-tumor effects via the humoral-mediated antibody dependent cellular cytotoxic (ADCC) and complement dependent cytotoxic (CDC) immune pathways (DiLillo D J, Ravetech J V, Cancer Immunol Res 3:704-713, 2015), the understanding and discovery of potential humoral immune pathways that can be suppressed via tumor-induced or -produced factors (TIPS factors) has been less interrogated due to the unobvious mechanism(s) by which they can mediate immune suppression. The antibody-mediated humoral immune response is governed by the coordination of antibody-cell surface antigen engagement that in turn positions the antibody on the antigen epitope at a certain proximity to the cell surface. In cases where this positioning is optimal, cell surface bound antibodies may engage with Fc-gamma receptors on Natural Killer (NK) or myeloid/monocytic cells to initiate ADCC as well as engage with the C1q complement initiating protein to cause death of antibody-bound cells via the classical complement CDC pathway (Reuschenbach M, et al. Cancer Immunol Immunother 58:1535-1544, 2009). These effects have been observed during the development of several therapeutic antibodies such as rituximab, trastuzumab, cetuximab as well as a number of experimental antibodies (Zhou X, et al. Oncologist 13:954-966, 2008; Hsu Y F, et al. Mol Cancer 9:8, 2010; Spiridon C I, et al. Clin Cancer Res 8:1720-1730, 2002; Kline J B, et al. Eur J Immunol 48:1872-1882, 2018). Similarly, humoral responses have been shown to occur within a patient's own immune response to dysregulated and/or aberrantly growing cells in response to vaccines and those with indolent disease, yielding antibodies predominantly of the IgM class with anti-proliferative as well as humoral immune-mediated killing activities (Staff C, et al. J Clin Immunol 32:855-865; Branden S, et al. Cancer Res 63:7995-8005, 2003).

TIPS factors can be readily detected in patient sera using established assays, and therefore their levels can be conveniently monitored for the purpose of establishing prognosis and/or disease stage and recurrence. Recent findings have shown that TIPS factors such as MUC16/CA125 (referred to as CA125 herein) may suppress humoral immune responses by directly binding to antibodies and perturbing the Fc region, thus making it less effective at engaging with Fc-gamma activating receptors FCGR2A or FCGR3A on immune cells and/or complement-mediating proteins, including C1q. Several of these data come from clinical studies of anti-cancer antibodies that rely on immune-effector mechanisms for their pharmacologic activity. Serum CA125 levels have been found to correlate with clinical outcome in a number of reported cases. These include reports on the experimental farletuzumab antibody in ovarian cancer and amatuximab antibody in mesothelioma (Vergote I, et al. J Clin Oncol 34:2271-2278, 2016; Nicolaides N C, et al. Cancer Biol Ther 13:1-22, 2018). Several reports have also shown the correlation of serum CA125 levels and shorter progression free survival (PFS) in patients with Hodgkin's and Non-Hodgkin's lymphoma, whereby patients with follicular lymphoma treated with rituximab plus CHOP (cyclophosphamide, doxorubicin (hydroxydaunomycin), vincristine (Oncovin® prednisolone) had a 31.4% improvement in 5-year PFS when CA125 levels were in the normal range (Prochazka V, et al. Int J Hematol 96:58-64, 2012). Moreover, CA125 was reported to be a prognostic factor in patients treated with standard chemotherapy who showed a 26.3% improvement in 3-year survival when their serum CA125 levels were within the normal range as compared to those with CA125 levels above the normal range (Bairey O, et al. Leumemia Lymph 44:1733-1738, 2003). There is a continuing need in the art to develop tools for discovering and analyzing the role of TIPS factors, their effects on TIPS-susceptible antibodies and a means for countering their negative effects in humoral immunity in cancer patients.

SUMMARY OF THE INVENTION

One aspect of the invention is a kit for characterizing an antibody comprising a Fab and a Fc domain. The kit comprises a first fluor-labeled protein or aptamer that specifically binds to the Fab domain of the antibody and a second fluor-labeled protein or aptamer that specifically binds to the Fc domain of the antibody. The first fluor and the second fluor participate in fluorescence resonance energy transfer (FRET) when bound to the antibody. Optionally, the kit further comprises the antibody.

In one aspect of the invention a kit is provided for characterizing a test antibody comprising a Fab and a Fc domain. The kit comprises a first fluor-labeled protein or aptamer that specifically binds to the Fab domain of the test antibody, and a second fluor-labeled protein or aptamer that specifically binds to the Fc domain of the test antibody. The first fluor and the second fluor participate in fluorescence resonance energy transfer (FRET) when bound to the test antibody.

In another aspect of the invention an antibody is provided that comprises a Fab and a Fc domain. The antibody is labeled with a first and a second fluor that participate in FRET. The first fluor is attached to an amino acid residue in the Fab domain and the second fluor is attached to an amino acid residue in the Fc domain.

In one aspect of the invention a kit for characterizing an antibody is provided. The antibody comprises a Fab and a Fc domain. The kit comprises an antibody labeled with a first fluor; and a protein or aptamer labeled with a second fluor. The first and second fluors participate in FRET when the protein or aptamer binds to the antibody. The first fluor is attached to an amino acid residue in the Fab domain and the protein or aptamer binds to the Fc domain, or the first fluor is attached to an amino acid residue in the Fc domain and the protein or aptamer binds to the Fab domain.

In yet another aspect of the invention a composition is provided that comprises an antibody and a first and second protein or aptamer. The antibody comprises a Fab and a Fc domain. The antibody is labeled with a first and a second fluor that participate in FRET. The first fluor is attached to an amino acid residue in the Fab domain and the second fluor is attached to a Fc-binding protein or aptamer.

Another aspect of the invention, a composition is provided that comprises an antibody that comprises a Fab and a Fc domain. The antibody is labeled with a first and a second fluor that participate in FRET. The first fluor is attached to a Fab binding protein or aptamer and the second fluor is attached to an amino acid in the Fc domain.

In still another aspect of the invention a method is provided for characterizing a dual-labeled antibody. A first fluor-labeled protein or aptamer and a second fluor-labeled protein or aptamer is contacted with the antibody to be characterized to form a ternary complex. The first fluor-labeled protein or aptamer binds to the Fab domain and the second fluor-labeled protein or aptamer binds to the Fc domain. The first and second fluors participate in FRET. Fluorescence resonance energy transfer (FRET) of the ternary complex is determined. The ternary complex is contacted with a tumor-induced or -produced factor (TIPS factor). FRET of the ternary complex in the presence of the TIPS factor is determined. The TIPS factor may be known or unknown.

In a further aspect of the invention a method is provided for characterizing an antibody. FRET of a dual-labeled antibody which comprises a Fab and a Fc domain is determined. The dual-labeled antibody is labeled with a first and a second fluor that participate in fluorescence resonance energy transfer (FRET). The first fluor is attached to an amino acid residue in the Fab domain and the second fluor is attached to an amino acid residue in the Fc domain. The dual-labeled antibody is contacted with a tumor-induced or -produced factor (TIPS factor). FRET of the dual-labeled antibody in the presence of the TIPS factor is determined. The TIPS factor may be known or unknown.

Another aspect of the invention is a method for characterizing a dual-labeled antibody. FRET of a dual-labeled antibody which comprises a Fab and a Fc domain is determined. The dual-labeled antibody is labeled with a first and a second fluor that participate in fluorescence resonance energy transfer (FRET). The first fluor is attached to an amino acid residue in the Fab or Fc domain and the second fluor is attached to a protein or aptamer that binds to the other domain. The dual-labeled antibody is contacted with a tumor-induced or -produced factor (TIPS factor). FRET of the dual-labeled antibody in the presence of the TIPS factor is determined. The TIPS factor may be known or unknown.

In one aspect of the invention, a method is provided for screening test substances for the ability to mitigate the effect of a tumor-induced or -produced factor (TIPS factor) on a TIPS-Susceptible Antibody (TSA). A TIPS-susceptible antibody is contacted with (a) a first fluor-labeled protein or aptamer that specifically binds to the Fab domain of the TIPS-susceptible antibody, (b) a second fluor-labeled protein or aptamer that specifically binds to the Fc domain of the TIPS-susceptible antibody, and (c) a TIPS factor to form a first complex. Fluorescence resonance energy transfer (FRET) of the first complex is measured. A TIPS-susceptible antibody is contacted with (a) a first fluor-labeled protein or aptamer that specifically binds to the Fab domain of the TIPS-susceptible antibody, (b) a second fluor-labeled protein or aptamer that specifically binds to the Fc domain of the TIPS-susceptible antibody, (c) a TIPS factor, and (d) a test substance, to form a second complex. Fluorescence resonance energy transfer (FRET) of the second complex is measured.

In another aspect of the invention a method is provided for screening test substances for the ability to mitigate an effect of a tumor-induced or -produced factors (TIPS factors) on a TIPS-susceptible antibody comprising a Fab and a Fc domain. The TIPS-susceptible antibody is contacted with the TIPS factor. The TIPS-susceptible antibody is labeled with a first and a second fluor that participate in FRET. The first fluor is attached to an amino acid residue in the Fab domain and the second fluor is attached to an amino acid residue in the Fc domain. A first complex is formed. FRET of the first complex is measured. The TIPS-susceptible antibody is contacted with the TIPS factor and a test substance, forming a second complex. FRET of the second complex is measured.

In another aspect of the invention a method is provided for screening test substances for the ability to mitigate the effect of a tumor-induced or -produced factors (TIPS factors) on a TIPS-susceptible antibody. A TIPS-susceptible antibody is labeled with a first and a second fluor that participate in FRET. The first fluor is attached to an amino acid residue in the Fab or Fc domain and the second fluor is attached to a binding protein or aptamer to the other domain. The dual-labeled test antibody is contacted with a TIPS factor to form a complex. The TIPS-susceptible antibody comprises a Fab and a Fc domain. The antibody FRET of the first complex is measured. A TIPS-susceptible antibody is contacted with a TIPS factor and a test substance, to form a second complex. FRET of the second complex is measured.

In still one more aspect of the invention, a method is provided for characterizing an antibody or for characterizing a pair of proteins or aptamers that bind to an antibody. The antibody is contacted with a first protein or aptamer that specifically binds to the antibody in its Fab domain. The first protein or aptamer is attached to a solid support, to link the antibody to the solid support. The antibody linked to the solid support is contacted with a second protein or aptamer that specifically binds to the test antibody in its Fc domain. The second protein or aptamer is labeled with a detectable label. The amount of the detectable label linked to the solid support is determined. The antibody linked to the solid support is contacted with the second protein or aptamer that specifically binds to the test antibody in its Fc domain, in the presence of a tumor-induced or -produced factors (TIPS factors). The amount of detectable label linked to the solid support in the presence of the TIPS factor is determined.

In yet another aspect of the invention, a kit is provided for characterizing a test antibody comprising a Fab and a Fc domain. The kit comprises a first protein or aptamer that specifically binds to the Fab domain of the test antibody. The first protein or aptamer is attached to a solid support. The kit also comprises a second protein or aptamer that specifically binds to the Fc domain of the test antibody. The second protein or aptamer is labeled with a detectable agent. Alternatively, the first protein or aptamer binds to the Fc domain and the second protein or aptamer binds to the Fc domain.

In one aspect of the invention a method is provided for identifying suitable pairs of protein or aptamer probes of antibody susceptibility to tumor-induced or -produced factors (TIPS factors). A pair of proteins or aptamers is tested for binding to an antibody and determining that both members of a pair can simultaneously bind. The pair of proteins or aptamers that are simultaneously bound to the antibody are tested for binding of the antibody to a cognate antigen of the antibody. Equivalent binding of the cognate antigen to the antibody in the presence and absence of the pair or protein or aptamers is determined.

In an additional aspect of the invention, a composition is provided that comprises a first fluor-labeled protein or aptamer that specifically binds to the Fab domain of an antibody, and a second fluor-labeled protein or aptamer that specifically binds to the Fc domain of the antibody to form a dual-labeled antibody. The first fluor and the second fluor participate in fluorescence resonance energy transfer (FRET) when bound to the antibody. One protein or aptamer may be protein A and one may be protein L. Alternatively, one may be protein A and one may be the cognate antigen to which the antibody binds. The antibody may be present in the composition.

In a further aspect of the invention a composition is provided that comprises an antibody, a first protein or aptamer that is bound to the antibody in its Fab domain, and a second protein or aptamer that is bound to the test antibody in its Fc domain. The first protein or aptamer is attached to a solid support. The second protein or aptamer is labeled with a detectable label. Alternatively, the first protein or aptamer is bound to the antibody in the Fc domain and the second protein or aptamer is bound to the antibody its Fab domain.

These and other aspects of the invention which will be apparent to those of skill in the art upon reading the specification provide the art with methods, compositions, and kits for use in improving anti-cancer antibody efficacy as well as anti-cancer therapeutic efficacy generally.

BRIEF DESCRIPTION OF THE DRAWINGS

FIG. 1. Schematic diagram of approximate positions of Fab/N-terminus and Fc/C-terminus domain paired probe sets to monitor antibody dynamic structure at steady-state and in the presence of TIPS factors. The figure indicates the approximate regions to which the antibody binding proteins Protein L (PL), Protein A (PA), Protein G (PG); the Fc Receptors (FcR or FcRn); the C1q complement initiating protein (C1q); the anti-Fab (αFab) and anti-Fc (αFc) aptamers; the anti-Fab (αFab) and anti-Fc (αFc) antibodies and antibody fragments; and the antibody-specific target antigen (antigen) bind, or to which fluors can be directly conjugated to amino acid (aa) residues within the Fab and/or Fc regions to generate a dual-labeled test antibody. The differing colors represent fluor 1 and fluor 2.

FIGS. 2A-2B. Identifying complementary Fab and Fc pairs via ELISA using rituximab, a human-rodent chimeric antibody that can bind the CD20 antigen or a peptide containing the rituximab binding epitope (Reff M E, et al. Blood 83:435-445, 1994). Briefly, 96-well ELISA plates were coated with CD20 peptide (FIG. 2A), Protein L (FIG. 2B) or no protein or peptide and incubated with rituximab, a non-binding control human IgG1, or bovine serum albumin (BSA); and probed with biotinylated-Protein G, -human FCGR1A, or -human FCGR3A; and secondarily probed with STRP-HRP. The results show examples of the compatibility that probes can have for dual binding to a test antibody.

FIG. 3. Effect of TIPS factors on dual-labeled test antibodies and probe selection. ELISA plates were coated with CD20 peptide (left set of bars), Protein L (middle set of bars) or BSA (right set of bars) and then probed with buffer (none), Protein G-biotin, FCGR1A-biotin or FCGR3A-biotin with or without the CA125 TIPS factor. Plates were washed and secondarily probed with streptavidin-HRP. As shown, the CA125 TIPS factor suppressed binding of the Fc domain probe FCGR3A-biotin in both the CD20 antigen and Protein L captured plate, while neither Protein G-biotin nor FCGR1A-biotin were affected, demonstrating and providing example of how the latter two sets are discovered to be appropriate for monitoring a dual-labeled test antibody's dynamic structure in the presence of a TIPS factor while FCGR3A is not.

FIGS. 4A-4B. Effect of TIPS factor on a dual-labeled test antibody with complementary probes to the Fab and Fc domains labeled with a covalently linked anti-FabAF488 and an anti-FcAF555 antibody, respectively. Briefly, the dual-labeled test antibody is incubated with TIPS factors or control proteins and tested for effects on antibody dynamic structure via energy exchange between the complementary AF488 and AF555 fluors and captured via FRET. FIG. 4A shows a fluorogram of the dual-labeled test antibody employed. FIG. 4B shows the effect of TIPS factor CA125 or control HSA proteins at 10 ng/mL on a covalently linked dual-labeled test antibody or covalently linked single-labeled anti-FabAF488 and anti-FcAF488 test antibodies that are added together in presence of TIPS factors and control proteins. $P<0.003$ FIGS. 5A-5C. Effect of TIPS factors on a dual-labeled test antibody covalently linked to Protein L-AF555 (PL555) probe at the N-terminus and a covalently linked Protein A-AF488 (PA488) probe to the same test antibody's C-terminus. Briefly, the dual-labeled test antibody is incubated with TIPS factors or control proteins and tested for effects on antibody dynamic structure via energy exchange between complementary Alexa fluors AF488 and AF555 and captured via FRET. FIG. 5A shows a fluorogram (left) of the AF555-labeled Protein L and a denaturing SDS-PAGE gel with unlabeled (left) or Alexa fluor labeled (right) Protein L (PL) and Protein A (PA) proteins. FIG. 5B shows a purified, dual-labeled test antibody covalently linked to PA488 and PL555 via NanoDrop One spectrophotometry/fluorometry with fluor peaks at 488 and 555 nm, respectively. FIG. 5C shows the effect of TIPS factor CA125 or control HSA proteins at 10 ng/ml on the covalently linked dual-labeled test antibody or covalently linked PL555 or PA488 single-labeled test antibodies alone or when added together in presence of TIPS factors or control proteins. These data demonstrate the ability of the dual-labeled test antibody to emit enhanced signal in the presence of TIPS factor but not control protein nor when test probe is single-label format. $P<0.006$ FIGS. 6A-6D. Effect of TIPS factor on dual-labeled test antibody with direct labeling of an amino acid residue with AF555 in the Fab domain and an AF488 fluor labeled Fc domain binding probe. Briefly, a dual-labeled test antibody is incubated with TIPS factors or control proteins and tested for effects on antibody dynamic structure via energy exchange between complementary fluors and captured via FRET. FIG. 6A is an ELISA demonstrating that a $NaN_3$-treated RTX-169-DBCO-biotin labeled antibody was bound by STRP-HRP while a $NaN_3$-treated RTX-WT-DBCO-biotin or untreated antibodies were not bound by STRP-HRP. A poly-lysine biotin-labeled RTX-169 (RTX-169-Bio full) served as a positive control for STRP-HRP binding. FIG. 6B demonstrates that the RTX-169-DBCO-biotin was labeled in the Fab domain where the unbound CYS 169 resides. Briefly, RTX-169-DBCO-biotin was papain digested, purified and the Fab and Fc domains were run on a nondenaturing SDS-PAGE gel and tested for STRP-HRP-biotin binding via western blot. As shown, STRP-HRP only bound the Fab fragment demonstrating the successful $NaN_3$-mediated click chemistry conjugation of the DBCO-biotin to the Fab domain. Full length RTX-169-DBCO-biotin and RTX-169 unlabeled antibodies served as positive and negative controls, respectively. Staining of the membrane showed equal amounts of Fab and Fc fragments (not shown). MW represents the molecular weight marker in kDa. FIG. 6C shows a fluorogram of the dual-labeled RTX-169 test antibody employed, whereby AF555 is conjugated to the mutated CYS 169 residue within the N-terminal region of rituximab (SEQ ID: NO 26 and 27) and is dual-labeled through the conjugation of PA488 to the C-terminus. FIG. 6D shows the effect of TIPS factor CA125 or control HSA proteins at 10 ng/mL on the dual-labeled test antibody or test antibody single-labeled with AF555 and a separate test probe labeled with PA488 when added together in the presence of test proteins, whereby the TIPS factor stimulated emission of the dual-labeled test antibody but not controls. P<0.008

DETAILED DESCRIPTION OF THE INVENTION

The inventors have developed methods, reagents, and compositions that are useful in the development of improved antibodies for treating cancers and other diseases where humoral mediated therapies are available. While not wanting to be limited to any particular theory or mechanism of action, applicants believe that certain tumor-induced or -produced factors (TIPS) bind to antibodies and alter their structure such that they are no longer able to bind to their cognate antigen or engage with other elements of the humoral immune system. These disruptions may include suppression of the protein-antibody FcR-Ab binding (antibody-Fc receptors on immune effector cells, such as Natural Killer (NK), macrophage, monocytes, etc.) and/or C1q-Ab (classical antibody-complement complex) and subsequent ADCC and/or CDC (antibody-target antigen binding and/or alternative complement-mediated killing) activity; suppression of effector cell activation upon Ab-FcR engagement via SIGLECS (sialic acid binding Ig-like lectin) receptors; and suppression of alternative complement pathway recognition protein binding.

In the assays taught and described below for measuring antibody binding to antigen or TIPS factors, any detectable label can be used. A fluorescent label is often convenient. Also useful are enzymatic, colorimetric, strong binding-pair, and radionuclear labels or agents. A detectable label may be immediately visible or detectable. Alternatively, it may require addition of other reagents to develop the detection. For example, a label can be an enzyme that requires particular substrates to make a product that is directly detected. Nonetheless, as referred to here, the enzyme itself is a detectable label, because it can be readily detected by treatment with the particular substrate. Similarly, a member of a strong binding pair may be used that is actually detected only when its directly-labeled binding partner is added. Biotin-streptavidin is just one of many examples of such a strong binding pair.

Some of the methods, compositions, and kits may be divided into three categories. In one category, an antibody, e.g., an anti-cancer antibody, is directly labeled, using two covalently attached fluors. One fluor is attached to the Fab or N-terminal domain and the other is attached to the Fc or C-terminal domain. The two fluors participate in FRET. In the second category, an antibody, e.g., an anti-cancer antibody, is bound by two proteins or aptamers that specifically bind to the antibody. The proteins or apatmers are labeled with a pair of fluors that participate in FRET. In the third category, one protein or aptamer is used and the antibody may have a unique amino acid engineered into its primary amino acid sequence that can be linked to a complementary fluor (see FIG. 6). In all categories, a change in FRET emission that occurs between the two fluors, whether to a protein or aptamer or attached directly to the antibody, indicates a change in the relationship of the two parts of the antibody molecule. Such a change can be used to detect and/or measure the effect of a TIPS factor on an anti-cancer antibody. Similarly, it can be used to measure the change in an antibody upon binding to its cognate antigen (also called its target antigen). A change in emissions can be determined as change in the intensity of emissions. Typically a change is determined when it is more than the amount that occurs using controls that do not cause a change in the antibody structure.

Examples of proteins that may be used to bind to the Fc domain of a human antibody are Protein A, Protein G, human FCGR1A, FCGR2A, FCGR2B, FCGR2C, FCGR3A, FCGR3B, FCGRT, FCRL5, mouse FCGR4, and human C1q. A protein that may be used to bind to the Fab domain of an antibody is Protein L or the antibody's natural antigen. Antibodies raised against the test antibody's Fab or Fc domain are also examples of domain specific protein probes.

Anti-cancer antibodies can be antibodies that are collected from a patient to be treated, collected from a different patient, or made in the laboratory by other means. Patient antibodies may be modified by various means prior to use. Certain commercial or experimental anti-cancer antibodies that may be analyzed using the methods of the invention include without limitation, rituximab, trastuzumab, trastuzumab emtansine, cetuximab, YP219, ocrelizumab, daratumumab, elotuzumab, alemtuzumab, necitumumab, pertuzumab, obinutuzumab, nivolumab, ipilimumab, pembrolizumab, ofatumumab, panitumumab, ibritumomab tiuxetan, sacituzumab govitecan, brentuximab vedotin and tositumomab.

Figure 3:
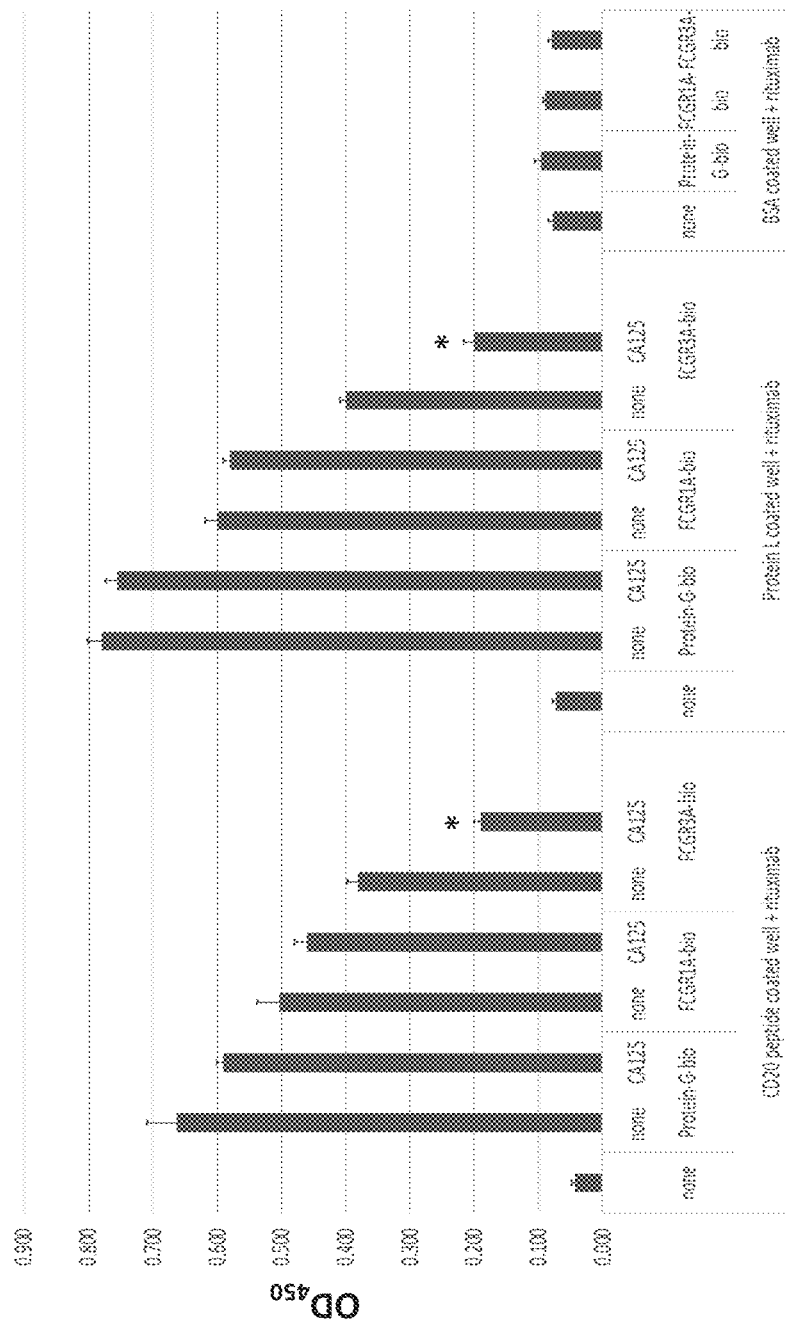

As shown in FIG. 3, a desirable a pair of proteins or aptamers that bind to an antibody desirably bind and remain bound to the antibody in the presence of antigen. Further, a desirable pair of proteins or aptamers also bind and remain bound to the antibody in the presence of a TIPS factor. This can be achieved with or without the use of crosslinking agents known by those skilled in the art.

Once a dual-labeled antibody or a pair of proteins or aptamers that bind to an antibody is appropriately identified, they can be used to identify an antibody whose dynamic structure is altered by the presence of a TIPS factor. Such an antibody is termed a TIPS-Susceptible Antibody (TSA). With these components in place, one can test one or more substances, whether natural or synthetic, pure compounds or mixtures, or natural extracts, for example, to identify a substance that mitigates, ameliorates, or reverses the change in the antibody induced by the TIPS factor. Test substances may be found in collections or libraries that are commercially available, for example.

Compositions of the invention can be formed in the course of conducting the methods. They may be pre-formed and packaged and provided to an entity that has a substance library to screen, for example. Similarly, the components of the assays and methods described here may be packaged together in a container and sold as a kit. The components of a kit need not be, but may be mixed together. They can be provided in separate containers or in a divided container, for example. Any selection of antibodies, pairs of proteins or aptamers that bind to an antibody, labeled antibodies, TIPS factors, buffers, solid supports, and labels, described here may be formed as a composition or kit.

While a few antibodies susceptible to one of potentially many TIPS factors are known, e.g., CA125, technologies that can identify these factors and TIPS Susceptible Antibodies (TSAs) whose dynamic structure is altered leading to suppressed humoral immune and pharmacologic activities to these effects are still needed.

The "dynamic structure" of an antibody or protein is defined as the three-dimensional structures of an antibody at a given time point, wherein such time point coincides with said antibody's engagement with another protein or agent, and the structure of said antibody before this time point has changed into a different structure after this time point in response to the antibody's engagement with another protein or agent. The effect of a TIPS factor (protein or non-protein) binding to an antibody and affecting its dynamic structure has been reported in the case of hapten binding to the CDR domains of antibodies that in turn allosterically alter their Fc domain, thereby reducing its engagement with Fc Receptors (Janda A, et al. Front Microbiol 7:22, 2016). Previous studies also have shown that the dynamic structure of the $(Fab')_2$ domain is affected when an antibody was bound to its antigen (Werner T C, et al. Proc Natl Acad Sci 69:795-799, 1972). Recently, Kline et al reported that while several humanized monoclonal $IgG_1$-type antibodies have similar amino acid structure, there are profound differences in the ability of a TIPS factor such as CA125 to bind them, suggesting either primary or secondary structure may dictate TIPS factor-antibody binding (Kline J B, et al. OncoTarget 8:52045-52060, 2017). In light of growing evidence that tumors utilize various pathways to avoid host immune defense and the fact that antibody-based approaches continue to be pursued against various cancer types, it is important to define methods to determine which antibodies are susceptible to TIPS factor binding that may result in structural dynamic change that can affect their engagement with humoral immune mechanisms and/or other functions as discussed here. These methods in turn enable the selection of lead antibodies from an antibody library based on resistance to TIPS factor suppressive effects and/or a means to identify said TIPS factor for patient screening. For example, if a test antibody is found to be affected by one or more TIPS factors, one may prescreen patients to avoid treating those that express a specific TIPS factor. Any preclinical-stage antibody may be used to screen patient samples for the presence of a specific TIPS factor as part of a drug development plan prior to full development, thereby saving the developers time in avoiding the costly investment required to develop an antibody that may be a TSA.

We provide probes, kits and methods for screening an antibody's dynamic structure in the presence of known and unknown TIPS factors that can affect antibody dynamic structure and suppress its downstream immune-effector function(s) and/or cellular internalization upon binding to its target cell surface target antigen. The methods include a step of composing and employing matched or complementary probes that can simultaneously bind to the N-terminus or Fab domain and the C-terminus or Fc domain of a given test antibody, not affect the antibody's ability to bind to its natural target antigen and be formatted in a way that can determine a change in spatial distances of said probes in the presence of a TIPS factor derived from tumor membrane and/or as a soluble factor as compared to antibody alone. The probes (or "agents") may comprise labeled antibody binding proteins such as Protein L and Protein A or G that are known to bind to the N- and C-termini of antibodies. Probes can also include labeled monoclonal antibodies (mAbs) and/or aptamers that specifically bind to the N- and C-termini of the test antibodies. Probes may also comprise a label-modified, antibody-specific antigen that when used in conjunction with a C-terminal probe (that may or may not be a natural Fc binding protein such as a Fc-gamma receptor or C1q) may define an antibody's dynamic structure alone or in the presence of a TIPS binding factor. These factors can be used in conjugated or non-conjugated formats to the test antibody. Finally, probes can be an antibody in which N-terminal and C-terminal residues are modified to support site-specific labeling of a said antibody with acceptor-donor probes that can monitor the dynamic structure of the test antibody in the presence of soluble or membrane bound TIPS factors as shown in FIG. 6.

FIG. 1 provides a schematic example of probes and their approximate binding regions. Probes comprising conjugated paired dyes or fluors may be used to measure the spatial distance of the N- and C-termini of a test antibody. These probes may be used in fluorescence resonance energy transfer (FRET) analysis whereby a fluorophore (donor) in an excited state from one probe transfers energy to a neighboring fluorophore (acceptor) of the complementary probe through dipole-dipole interaction, permitting one to measure the molecular proximity of the test antibody's N- and C-termini at Ångstrom distances. An increase or decrease of signal between test antibody alone versus test antibody plus TIPS factor suggest a binding and perturbation of the test antibody's dynamic structure and function.

In one method for measuring the dynamic state of an antibody as a function of distance change between the test antibody's N- and C-termini, the antibody is first incubated with paired probes (labeled or unlabeled with a detectable agent) that can simultaneously bind to antibody, not affect the test antibody's binding to its antigen nor have a probe displaced by a TIPS factor upon its binding to test antibody. This can be achieved by any method capable of measuring probes in a sandwich format including ELISA. Such paired probes can then be labeled with detector agents (such as but not limited to fluors, enzymes, radionuclides, etc.) to effectively monitor the N- and C-terminal distance of said test antibody in solution alone as compared to antibody in solution with soluble or membrane-bound TIPS. In some aspects, the probes comprise antibody-binding proteins or derivatives thereof that include:

(a) N-terminal (Fab domain) binding proteins or derivatives including Protein L (SEQ ID NO:1), a Fab specific antibody or antibody fragment, or the test antibody's specific antigen:

(b) C-terminal (Fc domain) binding proteins or derivatives including Protein A (SEQ ID NO: 2), Protein G (SEQ ID NO: 3), a Fc specific antibody or antibody fragment:

(c) Immunoglobulin Fc receptors (bind the Fc domain) of human FCGR1A (SEQ ID NO: 4), FCGR2A (SEQ ID NO:5), FCGR2B (SEQ ID NO:6), FCGR2C (SEQ ID NO:7), FCGR3A (SEQ ID NO:8), FCGR3B (SEQ ID NO:9), FCGRT (SEQ ID NO:10), FCRL5 (SEQ ID NO:11), mouse FCGR4 (SEQ ID NO: 12), human C1q (SEQ ID NO:13) and/or derivatives thereof.

The paired probes may comprise aptamer pairs that can specifically and simultaneously bind to the N- and C-termini of an antibody and do not affect test antibody binding to its antigen where said aptamers are labeled with a donor and acceptor detector agent (i.e., fluorophore (fluor), enzyme, radionuclide, etc) and tested for N- and C-termini proximity when bound to a test antibody alone or in the presence of potential soluble or membrane TIPS factors. TIPS factors that bind and "affect" the spatial distance of the complementary probes are identified as potential factors that impose suppression of humoral response(s) including pharmacokinetic (PK), pharmacodynamic (PD) and pharmacologic (PL) suppression, including cellular internalization or antigen binding of test antibody. The term "affect" generally refers to a 8% or greater change in signal of paired probes when incubated with test antibody alone as compared to antibody with TIPS factor. It may, depending on the antibody and the probes used also refer to a change of at least 5%, 15%, 20%, 25%, 30%, 35%, 40%, 45%, 50%, 55%, 60%, 70%, or 75%.

In some aspects of the compositions and methods, donor and acceptor detector agents linked to paired probes comprise Alexa fluors (AF):

| Alexa Fluor Dye | Absorption Max (nm) | Emission Max (nm) | Emission Color |
| --- | --- | --- | --- |
| Alexa Fluor 350 | 346 | 442 | Blue |
| Alexa Fluor 405 | 402 | 421 | Blue |
| Alexa Fluor 430 | 434 | 539 | Yellow-green |
| Alexa Fluor 488 | 495 | 519 | Green |
| Alexa Fluor 514 | 518 | 540 | Green |
| Alexa Fluor 532 | 531 | 554 | Yellow |
| Alexa Fluor 546 | 556 | 573 | Orange |
| Alexa Fluor 555 | 555 | 565 | Orange |
| Alexa Fluor 568 | 578 | 603 | Red-orange |
| Alexa Fluor 594 | 590 | 617 | Red |
| Alexa Fluor 610 | 612 | 628 | Red |
| Alexa Fluor 633 | 632 | 647 | Far-red |
| Alexa Fluor 635 | 633 | 647 | Far-red |
| Alexa Fluor 647 | 650 | 668 | Far-red |
| Alexa Fluor 660 | 663 | 690 | Near-IR § |
| Alexa Fluor 680 | 679 | 702 | Near-IR § |
| Alexa Fluor 700 | 702 | 723 | Near-IR § |
| Alexa Fluor 750 | 749 | 775 | Near-IR § |
| Alexa Fluor 790 | 782 | 805 | Near-IR § |

Yet in other aspects of the methods donor and acceptor detector agents comprise fluors:

| Fluor | Absorption/ Emission (nm) |
| --- | --- |
| Coumarin (AMCA) | 346/442 |
| Cy2 or Fluorescein (FITC) | 495/519 |
| Cy3 or Tetramethylrhodamine (TRITC) | 555/565 |
| Rhodamine Red | 587/603 |
| Texas Red | 590/617 |
| Cy5 | 650/668 |
| Cy5.5 | 679/702 |
| Cy7 | 749/775 |

Methods of screening for paired probes to test antibodies comprising Fab and Fc domains may comprise testing probes for: (1) ability to bind test antibody and not affect said antibody's ability to bind its target antigen; and (2) ability of both probes to stay bound by test antibody in the presence of known candidate or unknown TIPS factors. Probe pairs meeting these specifications may then be labeled with detector agents that can measure antibody dynamic structure in the presence of known or unknown TIPS.

Bispecific (BSP) antibodies may be screened for those that may be affected by soluble or membrane bound TIPS factors that may alter their PK, PD and/or PL activity, including inability to bind one or both of test antibody's target antigen(s). The BSP may be probed with N- and C-terminal paired probes and tested for dynamic structure in the presence or absence of soluble or membrane-bound TIPS factors. The BSP test antibody-specific antigens may be labeled with acceptor/donor detector agents (i.e., fluors, enzymes, radionuclides, etc.) and the dynamic structure may be tested to antigen bound BSP in the presence or absence of soluble or membrane TIPS. Those "affected" may then be tested for pharmacokinetic (PK), pharmacodynamics (PD) and pharmacological (PL) activity in presence of binding TIPS factors.

Methods for screening antibody drug conjugates (ADCs) that may be affected by soluble or membrane bound TIPS factors that may alter their PK, PD or PL activity, include cellular internalization. The ADC may be probed with N- and C-terminal probes and tested for dynamic structure in the presence or absence of soluble or membrane-bound TIPS. Those "affected" may then be tested for PK, PD and PL activity, including cellular internalization in presence of binding TIPS factors.

Labeled paired probes may be added to the test antibody in the presence of a crosslinking agent.

Protein L may be conjugated to the Alexa fluor AF555 and used in combination with Protein A conjugated to AF488.

An engineered rituximab (SEQ ID NO: 26 and 27) may be generated to have an unpaired cysteine in its Fab domain and used to directly conjugate a fluor, which includes but is not limited to AF555. The engineered antibody may then be then conjugated to a Protein A labeled with AF488 and used to monitor the binding of TIPS factor to test antibody.

Various terms and terminology ("terms") relating to aspects of the enclosed description are used throughout the specification and claims of this document. Such terms are to be given their ordinary meaning in the art unless otherwise specifically indicated. Other specifically defined terms are to be construed in a manner consistent with the definitions provided.

As used in this specification and the appended claims, the singular forms of "a," "an," and "the" also include plural references unless the content clearly specifically dictates otherwise. Reference to "a probe" may include combination of a pair of complementary probes capable of measuring the distance between two probes via any analytical method known by those skilled in the art. Similarly, reference to "a cell" may include a combination of two or more cells, and the like.

The term "about" as used when referring to a quantified values such as an amount, a period of time, molecular distance, and/or the like, is meant to encompass variations of up to ±8% from the specified value, as such variations are appropriate to carry out the disclosed methods. Unless otherwise indicated, all values expressing quantities of reagents, such as molecular weight, molarity, reaction conditions, molecular distance and so forth used in the specification and claims are to be understood as being quantified in all instances by the term "about." Accordingly, unless indicated to the contrary, the numerical values as set forth in the following specifications and listed claims are approximations that may vary depending upon the desired properties of the composition agent and/or methods sought to be obtained by the present invention. At the very least, each numerical value should at least be valued by the reported significant digits and through ordinary rounding methods known by those skilled in the art.

The term "antibody" (also referred to as "Ab") as used is meant in a broad sense and includes immunoglobulin (also referenced as "Ig") or antibody molecules including polyclonal antibodies (also referenced as pAbs), monoclonal antibodies (also referenced as mAbs) including murine, rat, monkey, human, humanized and chimerized mAbs, bispecific antibodies (also referenced as BSP), antibody drug conjugates (also referenced as ADCs), antibody fused imunotoxins and antibody fragments. In general, antibodies are proteins or polypeptide chains that bind to a specific antigen. An antigen is a structure that is specifically recognized by a given antibody. Canonical antibodies comprise heterotetramer glycosylated proteins, composed of two light chains and two heavy chains lined through a complex of disulfide and hydrogen bonds. Each heavy chain has a variable domain (variable region) (VH) followed by a number of constant domains (referred to as the Fc domain). Each light chain has a variable domain (VL) as well as a constant domain; the constant domain of the light chain is aligned with the first constant domain of the heavy chain and the light chain VL is aligned with the variable domain of the heavy chain. Antibody light chains of any species are assigned to one of two distinct types based on their amino acid sequences within their constant domains, namely kappa (κ) and lambda (λ). For compositions included herein, reference to light chain involves either subtype.

Immunoglobulins are categorized as classes or isotypes, depending upon the type of Fc domain namely IgA, IgD, IgE, IgG and IgM, which depend on the sequences contained within their heavy chain constant domain. The IgA and IgG isotypes are further comprised of subclasses as the isotypes $IgA_1$, $IgA_2$, $IgG_1$, $IgG_2$, $IgG_3$ and $IgG_4$. For compositions included herein, reference to heavy chain involves any subtype.

An immunoglobulin light or heavy chain variable region consists of a "framework" region interrupted by three Complementarity Determining Regions (CDRs) also referred to as "antigen-binding sites" based on sequence variability as reported (Wu T T, Kabat E A. J Exp Med 132:211-250, 1970). In general, an antigen-binding site is composed of six CDRs with three located within the variable heavy chain (CDRH1, CDRH2, CDRH3), and three within the variable light chain (CDRL1, CDRL2, CDRL3) (Kabat E A, et al. $5^{th}$ Ed. PHS, National Institutes of Health, Bethesda, Md., 1991).

Antigen-binding or antibody binding fragments are any structure that may exhibit binding affinity for a particular antigen. Some fragments are composed of portions of antibodies that retain antigen-binding specificity of the parent antibody molecule. In some instances, fragments may comprise at least one variable region (either a heavy chain or light chain variable region) or one or more CDRs of an antibody known to bind to a particular antigen that may be complexed with a variable region of another antigen, remain in single chain format or formatted as a peptide to retain binding to target antigen. Examples of fragments include, without limitation bispecific, diabodies and single-chain molecules as well as Fab, (Fab')$_2$, Fc, and single chain (ScFv) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like. Any antibody isotype may be used to produce an antibody or antigen-binding fragments. Additionally, fragments may include non-antibody proteins consisting of frameworks that may successfully incorporate polypeptide segments in an orientation that confers affinity for a given antigen of interest, such as protein scaffolds derived from adhesion-type proteins including the fibronectins and collagens. Antigen-binding fragments may comprise non-protein scaffolds such as aptamers. Aptamers may comprise nucleic acids, such as RNA, DNA, or nucleic acids with non-classical nucleotides, for example. The phrase "an antigen-binding fragment thereof" may be used to denote that a given antigen-binding fragment incorporates one or more antigen-binding segments of the antibody binding fragment referred to in the phrase. An antibody-fragment may also be referred to as a "probe."

"Specific binding" or "specifically binds" refers to the binding of an antibody, antibody fragment, antigen-binding fragment or aptamer to an antigen (including sequences contained within an antibody itself) with greater affinity than for other antigens. Typically, a specific antibody, antigen-binding fragment or aptamer binds target antigen with an equilibrium dissociation constant $K_D$ of about $9\times10^{-8}$ M or less.

An "antibody derivative" means an antibody, as defined above, that is modified by covalent attachment of another molecule such via peptide chemistry (i.e., amidation, etc.), chemical conjugation, genetic fusion and/or via post translational moieties (i.e., glycosyl, acetyl and/or phosphoryl) not typically associated with the antibody, and the like.

The term "antibody dynamic structure" refers to any change in structure that can affect the signal of two probes (i.e., antibody binding proteins (Protein L, A, G, etc; aptamers; natural mammalian binding proteins (i.e., Fc receptors, C1q, etc); Fab and Fc binding antibodies; haptens; and/or antibody specific antigens) that are attached to the antibody.

The term "monoclonal antibody (mAb)" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology but may also include recombinant methods.

"Fab domain" refers to any antibody sequence N-terminal to the antibody hinge disulfide region which is known by those skilled in the art.

"Fc domain" refers to any antibody sequence C-terminal to the antibody hinge disulfide region which is known by those skilled in the art.

An "antigen" is an entity to which an antibody, antibody fragment or aptamer specifically binds. This includes binding to a said antibody or protein of interest.

The term "tumor-induced or -produced factor (TIPS or TIPS factor)" refers to any protein or non-protein factor that is directly produced by a dysregulated cell or induced from normal cells by a dysregulated malignant cell. It has been reported that the CA125 protein is produced by dysregulated cells such as ovarian carcinoma and mesothelioma (Kline J B, et al. Eur J Immunol 48:1872-1882, 2018), as well as induced by lymphomas from normal surrounding epithelial cells (Sanusi et al. Perit Dial Int. 21:495-500, 2001).

The term "dysregulated cell" refers to any cell that behaves of functions differently than it normal counterpart. This includes transformed cells by pathogens as well as malignant cells derived from tumors.

The term "TIPS-inhibitor" refers to any protein or non-protein agent that can block a tumor-induced or -produced factor and/or a factor from a dysregulated cell from binding to test antibody.

The term "test antibody" refers to an antibody in which two probes have been attached, one to the Fab domain and the other to the Fc domain and screened to determine if test antibody is bound by TIPS factor and has an effect on its dynamic structure.

The term "CA125" refers to the TIPS gene product produced by MUC16 gene (HGNC: 15582; OMIM: 606154), which is found in soluble and membrane-bound forms. It has been reported to bind to antibodies and affect bound antibody humoral immune function (Kline J B, et al. Oncotarget 8:52045-52060, 2017).

The term "unknown TIPS" refer to TIPS that are not known to bind to antibody, BSP or ADC or whose composition is unknown at the time of screening.

The terms "cancer," "malignant," and "tumor" are well known in the art and refer to the presence of cells with -dysregulated cell growth and morphological features different than a normal cell type of similar origin. Malignant refers to those cancer cells capable of causing morbidity and/or mortality. As used, "cancer and tumor" includes premalignant and malignant types.

As used, the term "soluble" refers to a protein or non-protein agent that is not attached to the cellular membrane of a cell. For example, an agent that is soluble may be shed, secreted or exported from normal, dysregulated or cancerous cells into biological fluids including serum, whole blood, plasma, urine or microfluids of a tumor.

The term "labeled," with regard to a test antibody's binding agent (also referred to as a "probe"), is intended to encompass direct labeling of the probe by coupling (i.e., physically linking) a detectable substance to the probe (such as but not limited to a fluor, enzyme, radionuclide, etc.), as well as by indirect labeling of the probe by reactivity with another reagent that is directly labeled. An example of indirect labeling includes detection of a primary probe via a secondary fluorescently labeled probe that may include an antibody or aptamer that is specific to said probe. The primary or secondary probe may be labeled via radionuclides, chromophores, fluorophores, or enzymes. The probe or secondary probe may be an antibody derivative, an antibody fragment, a protein scaffold capable of target specific binding or an aptamer that is labeled with a protein ligand (e.g., biotin, the ligand for avidin and streptavidin).

The term "detector agent" or "detectable agent" refers to any agent that can be linked to a protein, a protein binding agent including aptamers and detected via devices commonly used in the field. These include but are not limited to fluors, enzymes and enzyme substrates, radionuclides, heavy metals and colorimetric dyes and substrates that can be detected via methods such as but not limited to densitometry, spectrophotometry, luminescence, microscopy, radiography and scintillation. Additional reagents may be needed to develop the detectable signal. The detector agent may be an alexa fluor AF555 covalently labeled Protein L.

The term "complementary fluor" refers to two fluorescent moieties in which one can act as an donor upon excitation at one wavelength to the second fluor agent that acts as an acceptor and emits specific wavelength signal and intensity that is proportional to the absolute distance of the two fluor agents and is commonly used in FRET-based assays by those skilled in the art. This can be any combination of donor and acceptor fluors.

The "level" of a specified protein or non-protein agent, as used, refers to the level or levels of the agent as determined using any method known in the art for the measurement of protein and/or non-protein agent levels in vitro or in vivo. Such methods include gel electrophoresis, capillary electrophoresis, high performance liquid chromatography (HPLC), thin layer chromatography (TLC), hyperdiffusion chromatography, fluid or gel precipitation reactions, absorption spectroscopy, colorimetric assays, spectrophotometric assays, flow cytometry, immunodiffusion (single or double), solution phase assay, immunoelectrophoresis, Western blotting, radioimmunoassay (RIA), enzyme-linked immunosorbent assays (ELISAs), immunofluorescent assays, fluorescence resonance energy transfer (FRET), Förster resonance energy transfer, electrochemiluminescence immunoassay, and the like. The level of an TIPS factor (e.g., CA125) may be determined using probe-based techniques, as described in more detail.

The term "dual-labeled test antibody" refers to one in which a fluor is attached directly or indirectly to a residue(s) in the Fab domain and a complementary fluor to residues in the Fc domain.

The term "TIPS susceptible antibody (TSA)" refers to any antibody, antibody fragment, BSP or ADC that is directly bound by a TIPS factor whose dynamic structure is altered. It has been reported that the CA125 TIPS factor, which is produced by malignant cells such as ovarian carcinoma and mesothelioma (Nicolaides N C, et al. Cancer Biol Ther 19:622-630, 2018) as well as induced by lymphomas from normal surrounding epithelial cells (Sanusi et al. Perit Dial Int. 21:495-500, 2001), can bind certain antibodies and alter their dynamic structure thus affecting their biological activities including ADCC, CDC, opsonization, internalization and/or PK profiles.

The term "antibody drug conjugate (ADC)" refers to any antibody that is conjugated or fused to a chemical or polypeptide that has toxic activity to cells.

The term "bispecific antibody (BSP)" refers to any antibody that can bind two or more different antigens. A BSP can comprise at least but not limited to two full length antibodies, a full length antibody and a single chain antibody, or two single chain antibodies, whereby one each binds to different antigens or different epitopes on the same antigen.

The term "antibody dependent cellular cytotoxicity (ADCC)" refers to a process where an antibody can bind to an antigen on a surface of a cell then engage with immune cells via sequences within said antibody's Fc domain that in turn results in immune cells releasing toxins that can kill bound cell.

The term "complement dependent cytotoxicity (CDC)" refers to a process where an antibody can bind to an antigen on a surface of a cell then engage with the C1q protein via sequences within said antibody's Fc domain that in turn results in initiation of classical complement cascade that can kill bound cell.

The term "internalization" refers to a process where an antibody, antibody fragment or ADC can bind to an antigen on a surface of a cell then internalize via mechanisms known to those skilled in the art.

The term "pharmacokinetic (PK)" refers to the time that an antibody maintains its steady state concentration when administered to a subject.

The term "pharmacodynamic (PD)" refers to the study of the biochemical and physiological effects of an antibody-based drug and its mechanisms of action(s), including the correlation of their actions and effects with their biochemical structure when administered to a subject.

The term "pharmacologic (PL)" refers to the known effect an antibody has on a managing or killing a disease cell in vitro or in vivo.

The term "sample" refers to a collection of similar fluids, cells or tissues isolated from a subject, as well as fluids, cells or tissues present within a subject. Fluids may include biological fluids that include liquid solutions contacted with a subject or biological source, including cell and organoid culture medium, urine, salivary, lavage fluids and the like.

The term "control sample," as used, refers to any biologically or clinically relevant control sample, including, for example, a sample from a healthy subject not afflicted with a particular cancer type or a protein known not to bind test antibody.

The term "control level" refers to an accepted or predetermined level of a protein or non-protein agent that is used to compare with the level of the same agent in a sample derived from a subject or is the baseline of non-specific protein binding to test antibody.

As used, "a difference" between signal of an antibody in control vs being bound by a TIPS agent is generally any difference that can be statistically determined using statistical methods commonly used by those skilled in the art and at a minimum a difference of 8% or greater as compared to control. It may, depending on the antibody and the probes used also refer to a change of at least 5%, 15%, 20%, 25%, 30%, 35%, 40%, 45%, 50%, 55%, 60%, 70%, or 75%.

The term "inhibit" or "inhibition of" means to reduce by a statistically measurable amount, or to prevent entirely.

The term "functional," in the context of an antibody, antibody fragment or antibody containing moiety (i.e. BSP, ADC, etc.) to be used in accordance with the methods described, indicates that the antibody is capable of binding to antigen and/or is able to bind to and kill target cell in vitro or in vivo.

The term "target cell" refers to a cell or population of cells that expresses antigen for a specific antibody or antibody containing moiety. These can be derived directly from patients or be from cell lines.

The term "effector cell" refers to any cell that can bind to an antibody and induce a killing effect on target cell. These include but are not limited to NK cells, CD3+ T-cells, CD8+ T cells, monocytes, macrophages, dendritic cells etc.

The term "pharmaceutically acceptable" refers to a substance that is acceptable to administer to a patient from a pharmacological as well as toxicological aspect and is manufactured using approaches known by those skilled in the art. These include agents approved by a regulatory agency of the Federal or a state government or listed in the U.S. Pharmacopeia or other generally recognized pharmacopeia for use in animals and humans. The term "pharmaceutically compatible ingredient" refers to a pharmaceutically acceptable diluent, adjuvant, excipient or matrix vehicle with which an anti-cancer agent is administered. "Pharmaceutically acceptable carrier" refers to a matrix that does not interfere with the effectiveness of the biological activity of the active ingredient(s) and is nontoxic to the host.

The terms "effective amount" and "therapeutically effective" are used interchangeably and, in the context of administering a pharmaceutical agent at an amount that is sufficient to produce an enhanced clinical outcome in a patient. An effective amount of an agent is administered according to the methods described here in an "effective regimen." The term "effective regimen" refers to a combination of amount of the agent and dosage frequency adequate to accomplish an enhanced clinical outcome for a patient with a particular cancer who may be selected for a particular TIPS profile. Enhanced efficacy is an improved clinical outcome when a patient is administered an agent that is capable of overcoming morbidity better than a said parental compound or an agent that can enhance the clinical outcome of an effective regimen.

The terms "patient" and "subject" are used interchangeably to refer to humans and other non-human animals, including veterinary subjects, that receive a therapeutic agent treatment. The term "non-human animal or non-human" includes all vertebrates. In a preferred embodiment, the subject is a human.

The term "non-human" refers to all vertebrates excluding *Homo sapiens*.

"Therapeutic agents" are typically substantially free from undesired contaminants. This means that an agent is typically at least about 50% w/w (weight/weight) pure as well as substantially free from interfering proteins and contaminants.

The term "screening" may refer to testing of TIPS factors that can bind to a test antibody, antibody fragment or antibody containing moiety (i.e., BSP, ADC, single chain antibody, antibody fragment, etc.) using, e.g., two probes to the antibody that can monitor the distance between the two when bound to antibody, antibody fragment or antibody containing moiety when alone and when combined with potential TIPS or unidentified TIPS factors within fluids from patients or subjects. The term may be used in other contexts in which a large number of test elements is being assayed to determine which among the test elements has a certain property. Similarly it can be used to refer to the assaying of patient samples for those having a particular property.

Composition of Probes, Kits and Methods for Monitoring Antibody Dynamic Structure in the Presence of Tumor-Induced and/or -Produced Factors (TIPS)

Compositions of probes, kits and methods may be used for identifying susceptible antibodies to TIPS factors that may bind a test antibody and affect its dynamic structure [here referred to as TIPS Susceptible Antibody (TSA)] as well as for identifying tumor-induced or -produced factors (here referred to as TIPS) that may affect antibody dynamic structure, as well as methods of using probes and kits for detecting TSAs and/or known or unknown TIPS factors capable of binding antibodies. The method may involve the binding of two probes where one binds to the Fab domain and the other the Fc domain. The Fab binding probe is an aptamer specific to antibody N-terminal sequences, Protein L, a Fab-specific antibody, the test antibody's specific antigen, or a small chemical that can specifically conjugate to a natural or non-natural residue(s) in the Fab domain. The Fc binding probe may be an aptamer specific to C-terminal sequences, Protein A, Protein G, a Fc-specific antibody, a natural mammalian Fc binding protein (i.e. Fc receptors, FcRn, C1q, etc), or a small chemical or linker that can specifically conjugate to a natural or non-natural residue(s) in the Fc domain. Examples are schematically shown in FIG. 1 and experimentally shown in FIGS. 4-6. Kits may be composed of said probes that are able to detect a change in distance between N-terminal and C-terminal probes when a TSA is affected by a TIPS factor. Distance may be measured in angstroms and can be detected by any instrument capable of measuring signal of probes with detection labels used by those skilled in the art.

In the methods for identifying a TSA, a test antibody is added to a complementary set of Fab and Fc domain probes in presence of a candidate TIPS factor or unknown TIPS factors and signal is compared to dual-labeled test antibody plus probes alone to determine if candidate TIPS factors may change antibody dynamic structure by bringing probes closer or farther apart, thereby altering the signal produced between probes. Complementary probes refer to those that can be used in combination to detect a signal. For example, a Fab domain probe may be labeled with a fluor that emits energy when exposed to certain light wavelengths that in turn stimulate the signal of the Fc domain probe that contains a fluor capable of stimulated emission by the fluor contained Fab probe. These signals (wavelengths, enzymatic activity, temperature, etc.) can be captured by any machine or device that can detect a fluorescent, colorimetric, thermographic, luminescent or visual change in signal. If the test antibody is bound by a TIPS factor that results in altered antibody structure, the wavelength between two complementary probes will change thus signaling that the antibody is a TSA. A change of at least 8% is typically considered as being a meaningful effect on dynamic structure as it can perturb TSA ADCC and CDC functions. Depending on the antibody and the probes used a meaningful effect also may be defined as a change of at least 5%, 15%, 20%, 25%, 30%, 35%, 40%, 45%, 50%, 55%, 60%, 70%, or 75%.

For TIPS factor and TSA assessments, the sample tested for a known or unknown TIPS factor binding and subsequent TSA activity may be a purified protein or non-protein factor produced recombinantly, synthetically or derived from natural sources. Natural sources include whole blood, serum, plasma, pleural effusions, ascites, tumor tissues from surgical resection or biopsies, histological preparations, and the like. Alternatively, a protein fraction can be isolated from a dysregulated or malignant cell's soluble or membrane compartments and analyzed for TIPS factor binding and TSA effect on test antibody. For example, the step of determining if a TIPS factor has test antibody binding and TSA activity may involve labeling test antibody with N- and C-terminal complementary fluor probes, then determine its signal using FRET, comparing signal when antibody is alone or after mixture with a known or unknown TIPS factor. Generally, the antibody is either directly labeled with specific complementary dyes or fluors capable of producing a detectable signal as a dual labeled test antibody or bound by complementary N- and C-terminal probes. Examples of types of labels include enzyme labels, radioisotopic labels, nonradioactive labels, fluorescent labels, toxin labels and chemoluminescent labels. Many such labels are readily known to those skilled in the art. For example, suitable labels include, but are not limited to radiolabels, fluorescent labels [such as Alexa fluor 488 (AF488) or 555 (AF555)], epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorine dyes, oxazin dyes, phenanthridine dyes, rhodamine dyes, Alexa Fluor® dyes, and the like. Detection of a signal from the dual-labeled test antibody indicates that the TIPS factor has TSA activity, which is typically indicated by a signal change of 8% or greater between conditions. Depending on the antibody and the probes used the signal change may be at least 5%, 15%, 20%, 25%, 30%, 35%, 40%, 45%, 50%, 55%, 60%, 70%, or 75%.

The level of a TIPS factor with TSA activity in a biological sample can (but need not) be determined with respect to one or more standards. The standards can be historically or contemporaneously determined. The standard can be, for example, a biological sample known not to be cancerous from a different subject. The standard can also be the patient sample under analysis contacted with an irrelevant antibody known to be resistant to TSA activity.

The use of TIPS factor that can produce a TSA effect on the test antibody can also be formatted to screen for inhibitors that may bind a particular TIPS factor. The TSA may be labeled to produce a dual-labeled test antibody or with a complementary set of probes to the Fab (N-terminal) and Fc (C-terminal) domains and a TIPS protein is added to labeled TSA in the presence of a library of compounds and screened for inhibition of TIPS binding to TSA. A dual-labeled test antibody may be used to screen a compound library in the presence of a known TSA, where an inhibitory compound may block the signal of said TSA to test antibody. The library consists of small chemical compounds. The library may consist of peptides and/or proteins including antibodies and antibody fragments. The library may also comprise natural products, such as human or non-human-derived serum proteins, soil samples or plant extracts. Compounds found to block TIPS factor ability to bind TSAs via FRET or other assays are referred to as TIPS factor inhibitors.

In screening for TIPS factor inhibitors, a hybrid format may be used in which one of the detectable labels that participates in FRET is attached to an amino acid residue that is part of the antibody, in the Fab or the Fc domain, and one of the detectable labels that partipates in FRET is attached to a probe that binds to the Fab or Fc domain. Typically, the one of the two detectable labels is attached to the Fab domain and one to the Fc domain. When testing FRET of two labels, irrespective of how they are attached or bound to the domains of the antibody, one can test in the presence and absence of TIPS factor. The TIPS factor may bind to the antibody and change the FRET. When a potential TIPS factor inhibitor is contacted with the dual labeled antibody bound to a TIPS factor, FRET can again be measured. This measurement may be done in the presence and in the absence of the potential TIPS factor inhibitor. Similarly, the measurement may be done on the dual labeled antibody bound to a TIPS factor which has been contacted with the potential TIPS factor inhibitor and on the dual labeled antibody bound to a TIPS factor that has not been contacted with the TIPS factor inhibitor.

A cancer subject may be treated with a TIPS factor inhibitor. For example, a patient may have a mesothelin-expressing cancer such as colorectal, lung, ovarian, pancreatic, endometrial carcinoma or mesothelioma. Several anti-mesothelin antibodies have been reported to bind to TIPS factor, making a TIPS factor inhibitor a desirable entity.

A patient with mesothelin-expressing cancer that expresses a TIPS factor may be treated with a TIPS factor inhibitor. An anti-mesothelin therapeutic agent is administered to a subject along with the TIPS-inhibitor. The TIPS factor may be CA125. An anti-mesothelin therapeutic agent may be administered to the subject, where the subject has a baseline CA125 level that is above the normal range. The TIPS factor inhibitor may be administered alone. The TIPS factor inhibitor may be administered in combination with chemotherapy. The chemotherapy may be cisplatin, carboplatin and/or pemetrexed, or any other chemotherapeutic agents considered standard of care at the time when the subject is treated. CA125 expression level may be determined by any means known in the art.

An anti-mesothelin therapeutic agent may be an antibody that specifically binds to mesothelin, preferably to mesothelin expressed on mesothelioma, lung adenocarcinoma, or colorectal cells. Alternatively, antigen-binding fragments of such an antibody, derivatives, and variants may be used for treatment. An exemplary antibody that specifically binds to mesothelin may be an antibody selected from the group consisting of:

(a) an antibody comprising YP219 antibody CDRs: SEQ ID NO:14 (GFDLGFYFYAC) as CDRH1, SEQ ID NO:15 (CIYTAGSGSTYYASWAKG) as CDRH2, SEQ ID NO:16 (ARSTANTRSTYYLNL) as CDRH3, SEQ ID NO:17 (QASQRISSYLS) as CDRL1, SEQ ID NO:18 (GASTLAS) as CDRL2 and SEQ ID NO: 19 (QSYAYFDSNNWHA) as CDRL3, numbered according to Kabat;

(b) an antibody that binds the same epitope as YP218 (Zhang et al. Scientific Reports volume 5, Article number: 9928, 2015).

An antibody that specifically binds to mesothelin may comprise a mature light chain variable region comprising the amino acid sequences of SEQ IDS NO: 17, 18 and 19 and/or a mature heavy chain variable region comprising the amino acid sequences of SEQ IDS NO: 14, 15 and 16. The anti-mesothelin therapeutic agent may be YP219. Other useful antibodies that specifically bind to mesothelin comprise mature light and heavy chain variable regions having at least 90% and preferably at least 95%, 96%, 97%, 98% or 99% sequence identity to SEQ IDS NO: 17, 18 and 19, or SEQ IDS NO: 14, 15 and 16. Other useful anti-mesothelin antibodies or derivatives thereof can competitively inhibit binding of YP219 to mesothelin, as determined, for example, by immunoassay. A derivative of an anti-mesothelin antibody may also be used in the practice of present methods. Typical modifications to make such derivatives include, e.g., glycosylation, deglycosylation, acetylation, pegylation, phosphorylation, amidation, derivatization by known protecting/blocking groups, proteolytic cleavage, linkage to a cellular ligand or other protein, cytotoxic small molecule and the like. Additionally, the derivative may contain one or more non-classical amino acids.

The present methods can be combined with other means of treatment such as surgery (e.g., debulking surgery), radiation, targeted therapy, chemotherapy, immunotherapy, use of growth factor inhibitors, or anti-angiogenesis factors. An anti-mesothelin therapeutic agent along with a TIPS factor inhibitor can be administered concurrently to a patient undergoing surgery, chemotherapy or radiation therapy treatments. Alternatively, a patient can undergo surgery, chemotherapy or radiation therapy prior to or subsequent to administration of the anti-mesothelin therapeutic agent and TIPS factor inhibitor by at least an hour and up to several months, for example at least an hour, five hours, 12 hours, a day, a week, a month, or three months, prior or subsequent to administration of the anti-mesothelin therapeutic agent. Administration of a therapeutically effective amount of a platinum-based chemotherapy and/or a folate antimetabolite may be given to the subject in addition to the anti-mesothelin therapeutic and TIPS factor inhibitor agents. For example, administration of therapeutically effective amounts of an anti-mesothelin antibody, a TIPS factor inhibitor, a platinum-based chemotherapy, and/or a folate antimetabolite may be administered. The platinum-based chemotherapy may be cisplatin, carboplatin, oxaliplatin, satraplatin, picoplatin, nedaplatin, triplatin, lipoplatin, or combinations thereof. The platinum-based chemotherapy may be any other platinum-based chemotherapy known in the art. The folate antimetabolite is pemetrexed. The platinum-based chemotherapy may be administered to the subject once every week, once every two weeks, once every three weeks, or once every four weeks. The folate antimetabolite may be administered to the subject once every week, once every two weeks, once every three weeks, or once every four weeks. When both a folate antimetabolite and a platinum-based chemotherapy are administered to the subject as part of the treatment regimen, the anti-mesothelin therapeutic agent, the TIPS factor inhibitor, the platinum-based chemotherapy, and the folate antimetabolite may be administered sequentially in any order or simultaneously.

A subject may have received first-line surgical resection of the tumor, first-line platinum-based therapy, first-line folate antimetabolite-based therapy, and/or first-line platinum and folate antimetabolite-based therapy for treatment of a mesothelin-expressing cancer prior to administering anti-mesothelin antibody and TIPS factor inhibitor.

Administration of the therapeutic agents (including the anti-mesothelin therapeutic agent, the folate antimetabolite, and/or the platinum-based chemotherapy and TIPS factor inhibitor) may be by any means known in the art.

A therapeutic antibody may be used that comprises the CDR sequences that can direct binding of an antibody to the CD20 antigen: SEQ ID NO:20 (GYTFTSYN) as CDRH1, SEQ ID NO:21 (IYPGNGDT) as CDRH2, SEQ ID NO:22 (ARSTYYGGDWYFNV) as CDRH3, SEQ ID NO:23 (SSSVSY) as CDRL1, SEQ ID NO: 24 (ATS) as CDRL2 and SEQ ID NO:25 (QQWTSNPPT) as CDRL3, numbered according to IMGT. For example but not limited to, a patient may have a CD20-expressing cancer such as Hodgkin's, Non-Hodgkin's or follicular lymphoma. Previous reports have shown that anti-CD20 antibodies are bound by TIPS factors, making a TIPS factor inhibitor a desirable entity.

A patient with CD20-expressing cancer that expresses a TIPS factor may be treated with a TIPS factor inhibitor. An anti-CD20 therapeutic agent may be administered to a subject along with the TIPS factor inhibitor. The TIPS factor may be CA125. An anti-CD20 therapeutic agent may be administered to the subject, where the subject has a baseline CA125 level that is above the normal range. The method may involve administering the TIPS factor inhibitor alone. Alternatively, the TIPS factor inhibitor may be administered in combination with chemotherapy. The chemotherapy may be the combination of CHOP (cyclophosphamide, doxorubicin (hydroxydaunomycin), vincristine (Oncovin®), and prednisolone) or any other chemotherapeutic agents and/or medical procedure considered standard of care at the time when the subject is treated. CA125 expression level may be determined by any means known in the art.

Various delivery systems may be used to administer the therapeutic agents (including the anti-mesothelin or anti-CD20 therapeutic agent, the folate antimetabolite, the platinum-based, and/or CHOP chemotherapy or TIPS factor inhibitor) including intradermal, intramuscular, intraperitoneal, intravenous, subcutaneous, intranasal, epidural, and oral routes as deemed necessary. The agents may be administered, for example by infusion or bolus injection, by absorption through epithelial or mucocutaneous linings (e.g., oral mucosa, rectal and intestinal mucosa, and the like) via systemic or local approaches.

The therapeutic agents may be administered by injection via syringe, catheter, suppository, or any implantable matrix or device.

The therapeutic agents and pharmaceutical compositions may be administered orally in any acceptable dosage form such as capsules, tablets, aqueous suspensions, solutions or the like.

Preferred methods of administration of the therapeutic agents include but are not limited to intravenous injection and intraperitoneal administration at a final concentration suitable for effective therapy.

The TIPS factor inhibitor in combination with other drugs may be administered as pharmaceutical compositions comprising a therapeutically or prophylactically effective amount of the therapeutic agent(s) and one or more pharmaceutically acceptable or compatible ingredients.

The amount of the therapeutic agent that is effective in the treatment or prophylaxis of a cancer may be determined by standard clinical techniques. In addition, in vitro assays may optionally be employed to help identify optimal dosage ranges required for TIPS factor inhibitor. Effective doses may be extrapolated from dose-response curves of TIPS factor inhibitor derived from in vitro or animal model test systems.

For example, toxicity and therapeutic efficacy of the agents can be determined in cell cultures or experimental animals by standard pharmaceutical procedures for determining the $LD_{50}$ (the dose lethal to 50% of the population) and the $ED_{50}$ (the dose therapeutically effective in 50% of the population) values. The dose ratio between toxic and therapeutic effects is the therapeutic index and it may be expressed as the ratio $LD_{50}/ED_{50}$. Agents that exhibit large therapeutic indices are preferred. When an agent exhibits toxic side effects, a delivery system that targets the agent to the site of affected tissue may be used to minimize potential damage to non-mesothelin-expressing cells and, thereby, reduce side effects.

The dosing and dosage schedule may vary depending on the active drug concentration, which may depend on the needs of the subject.

Composition of Kits to Identify Tips Factors and Tips Susceptible Antibodies (TSA)

Further provided here are kits for making complementary probes to screen antibodies to determine their dynamic structure in the presence and absence of potential test antibody binding TIPS factors and for screening to identify TIPS factor inhibitors. The kits may contain a labeled fluorescent Protein L (SEQ ID NO: 1) labeled with a fluor, such as the one listed within this document, and a Protein A (SEQ ID NO: 2) or Protein G (SEQ ID NO:3) labeled with a complementary fluor that can be stimulated by the fluor bound to Protein L, a vessel for containing the Protein L, Protein A and/or Protein G when not in use, and instructions for using the paired probes for determining if a TIPS factor can affect the dynamic structure of a dual-labeled test antibody. The kit may have instructions on how to conjugate the Protein L and Protein A probes to effectively generate a dual-labeled test antibody. The instructions may specify that a baseline level of signal as determined by a fluorescent reading instrument and that a signal that is altered by at least 8% is indicative of the TIPS having an effect on test antibody, and said antibody being a TIPS Susceptible Antibody (TSA). Instructions may specify that a baseline signal change of 50% is indicative of a TIPS factor having an effect on test antibody. Alternatively, the instructions may specify that the probes may be added to 384 or 96 well microtiter plate formats to screen multiple TIPS factors simultaneously, wherein the TIPS factor may be from a biological fluid, primary or cultured tumor cells or an isolated protein or non-protein agent. Microtiter plates may also contain libraries of peptides, proteins, nucleic acids, natural products, and/or small chemical agents (here referred to as compounds) whereby the probes are added to a TSA in the present of TIPS factors and added to 384 or 96 well microtiter plates containing a said library to identify a compound that can block TIPS factor effect on TSA dynamic structure. A signal that is reduced or enhanced 8% or greater is indicative of a compound having TIPS factor inhibitor activity. One or more additional containers may enclose elements, such as reagents or buffers, which may be used in the assay(s). Such kits can also, or alternatively, contain a detection reagent that contains a reporter group suitable for direct or indirect detection of TIPS factor antibody binding.

Kits for making complementary aptamer-based probes may be used to screen test antibodies to determine their dynamic structure in the presence and absence of TIPS factor and for screening TIPS factor inhibitors. The kits contain a labeled fluorescent aptamer that can bind to an antibody Fab domain and not disrupt its ability to bind its antigen. The fluor can be any fluor, such as one from the list of fluors listed within this document, and a second aptamer that can specifically bind to an antibody Fc domain labeled with a complementary fluor that can be stimulated by the fluor bound to the Fab aptamer, a vessel for containing the Fab and Fc binding aptamers when not in use, and instructions for using the paired probes for determining if a TIPS factor can affect the dynamic structure of a dual-labeled test antibody. The instructions may include methods on how to chemically conjugate the aptamers to create an effective dual labeled test antibody. The instructions may specify that a baseline level of signal as determined by a fluorescent reading instrument and that a signal that is altered by at least 8% is indicative of TIPS factor having an effect on test antibody, and said antibody being a TSA. Instructions may specify that a baseline signal change of 50% is indicative of TIPS factor having an effect on test antibody. Alternatively, the instructions may specify that the probes may be added to 384 or 96 well microtiter plate formats to screen multiple TIPS factors simultaneously, wherein the TIPS factors may be from a biological fluid, primary or cultured tumor cells or an isolated protein or non-protein agent. The TIPS factor may be known or unknown. The microtiter plates may also contain libraries of peptides, proteins, nucleic acids, natural products, and/or small chemical agents (here referred to as compounds) whereby the probes are added to a TSA in the present of TIPS factor and added to 384 or 96 well microtiter plates containing a said library to identify a compound that can block TIPS factor effect on TSA dynamic structure where a signal that is reduced or enhanced 8% or greater is indicative as a TIPS factor inhibitor. One or more additional containers may enclose elements, such as reagents or buffers, to be used in the assay(s). Such kits can also, or alternatively, contain a detection reagent that contains a reporter group suitable for direct or indirect detection of TIPS factor antibody binding.

Kits may contain a labeled fluorescent antibody that can bind to a test antibody Fab domain and not disrupt its ability to bind its antigen. The fluor may optionally be selected from a list of fluors listed within this document. The kit may also comprise a second antibody that can specifically bind to an antibody Fc domain labeled with a complementary fluor that can be stimulated by the fluor bound to the Fab binding antibody, a vessel for containing the Fab and Fc binding antibodies when not in use, and instructions for using the paired probes for determining if a TIPS factor can affect the dynamic structure of a dual-labeled test antibody. The instructions may include optimal methods for chemically conjugating the anti-Fab and -Fc antibodies to test antibody to generate an effective dual-labeled test antibody probe. The instructions may specify that a baseline level of signal as determined by a fluorescent reading instrument and that a signal that is altered by at least 8% is indicative of the test antibody being a TSA affected antibody. Instructions may specify that a baseline signal change of 50% is indicative of a TSA antibody. Alternatively, the instructions may specify that the probes may be added to 384 or 96 well microtiter plate formats to screen multiple TIPS factors simultaneously, wherein the TIPS factor may be from a biological fluid, primary or cultured tumor cells or an isolated protein or non-protein agent. It may be known or unknown. The microtiter plates may also contain libraries of peptides, proteins, nucleic acids, natural products, and/or small chemical agents (here referred to as compounds or agents) whereby the probes are added to a dual-labeled test TSA antibody in the present of TIPS factors and added to 384 or 96 well microtiter plates containing a said library to identify a compound that can block TIPS factor effect on TSA dynamic structure where a signal that is reduced or enhanced 8% or greater is indicative as a TIPS factor inhibitor. One or more additional containers may enclose elements, such as reagents or buffers, to be used in the assay(s). Such kits can also, or alternatively, contain a detection reagent that contains a reporter group suitable for direct or indirect detection of TIPS factor antibody binding.

The kits may contain a labeled fluorescent antigen that is specifically bound by the test antibody in such a way that the label does not disrupt the test antibody's ability to bind to its antigen and is labeled with a fluor such as one listed within this document and a second probe that binds to an antibody Fc domain labeled with a complementary fluor that can be stimulated by the fluor bound to the antigen, a vessel for containing the antigen and Fc probe when not in use, and instructions for using the paired probes for determining if a TIPS factor can affect the dynamic structure of a dual-labeled test antibody. The Fc probes can be from a number of known Fc binding proteins including but not limited to human FCGR1A (SEQ ID NO:4), FCGR2A (SEQ ID NO: 5), FCGR2B (SEQ ID NO:6), FCGR2C (SEQ ID NO:7), FCGR3A (SEQ ID NO: 8), FCGR3B (SEQ ID NO:9), FCGRT (SEQ ID NO:10), FCRL5 (SEQ ID NO: 11), mouse FCGR4 (SEQ ID NO:12), human C1q (SEQ ID NO:13) and/or derivatives thereof, a Fc domain specific aptamer or Fc specific antibody or antibody fragment, Protein A or G. The instructions may specific the optimal means to chemically conjugate probes to test antibody to make an effective dual-labeled test antibody. The instructions may specify that a baseline level of signal as determined by a fluorescent reading instrument and that a signal that is altered by at least 8% is indicative of TIPS factor having an effect on a TSA. Instructions may specify that a baseline signal change of 50% is indicative of TIPS factor having an effect on test antibody. Alternatively, the instructions may specify that the probes may be added to 384 or 96 well microtiter plate formats to screen multiple TIPS factors simultaneously, wherein the TIPS factors may be from a biological fluid, primary or cultured tumor cells or an isolated protein or non-protein agent. The microtiter plates may also contain libraries of peptides, proteins and/or small chemical agents (here referred to as compounds) whereby the probes are added to a dual-labeled test TSA in the present of TIPS factors and added to 384 or 96 well microtiter plates containing a said library to identify a compound that can block TIPS factor effect on TSA dynamic structure where a signal that is reduced or enhanced 8% or greater and does not affect the antigen binding to test antibody is indicative as a TIPS factor inhibitor. One or more additional containers may enclose elements, such as reagents or buffers, to be used in the assay(s). Such kits can also, or alternatively, contain a detection reagent that contains a reporter group suitable for direct or indirect detection of TIPS factor antibody binding.

Kits may also comprise a mixture of Fab and Fc probes, for example using fluor labeled antigen in combination with fluor labeled Protein A, Protein G, an Fc specific antibody or antibody fragment, or a Fc binding protein. Another example is using a fluor labeled Protein L in combination with a fluor labeled Fc specific antibody or antibody fragment, or a Fc binding protein in conjugate or non-conjugate form. Yet another example may be a fluor labeled aptamer in combination with a complementary fluor labeled Fab or Fc binding protein.

Kits may also comprise an unlabeled complementary Fab probe (Protein L, aptamer, antigen, etc.) that can be used in ELISA format to capture test antibody and a second biotin or other detector capable label and unlabeled probe that can bind to test antibody Fc domain (Protein A, Protein G, Fc receptors, etc). This format is used for primary screening of TIPS factors to determine if they have an effect on Fc binding probes by: (1) coating ELISA plate with Fab probe, (2) adding test antibody, with or without TIPS and Fc-biotin probe to measure binding in presence or absence of TIPS factor. If no difference in Fc probe binding is observed between TIPS factor treated and control wells, then said probes are suitable for pairing. Finally, kit may contain biotinylating agent to label test antibody to determine ability of test antibody to bind antigen in the present of unlabeled Fab and Fc probes by: (1) coating wells with test antibody's antigen, (2) adding Fab and Fc probe to biotinylated test antibody and screening for antigen binding via secondary streptavidin-HRP. If no difference exists between antigen binding in presence of Fab and Fc probes as compared to test antibody alone, the probes are sufficient as pairs to test against TIPS factors and determine if test antibody is a TSA.

Kits also typically contain a label or instructions for use in the methods described here. The label or instruction refers to any written or recorded material that is attached to, or otherwise accompanies a kit at any time during its manufacture, transport, sale or use. It can be a notice in the form prescribed by a governmental agency regulating the manufacture, use or sale of pharmaceuticals or biological products, which notice reflects approval by the agency of manufacture, use or sale for human administration. The label or instruction can also encompass advertising leaflets and brochures, packaging materials, instructions, audio or videocassettes, computer discs, as well as writing imprinted directly on the pharmaceutical kits.

The above disclosure generally describes the present invention. All references disclosed here are expressly incorporated by reference. A more complete understanding can be obtained by reference to the following specific examples, which are provided here for purposes of illustration only, and are not intended to limit the scope of the invention.

Example 1—Developing Complementary Binding Pairs to Monitor for Tips Factor Binding to Dual-Labeled Test Antibody and Effect on their Dynamic Structure FIG. 1 shows a schematic diagram of an antibody structure and approximate regions where Fab/N-terminal and Fc/C-terminal specific probes may bind and be tested for their ability to be used in pairs to measure antibody dynamic structure. While many of these proteins have been shown to bind antibodies, the ability to use two simultaneously to monitor antibody dynamic structure in a high throughput and functional based assay is unknown. In particular, we teach methods on the how to identify and combine probes that may remain bound to a dual-labeled test antibody and not be displaced by a TIPS factor using chemical conjugation and screening to ensure such treatment does not affect test antibody binding to its antigen.

Figures 2A, 2B:
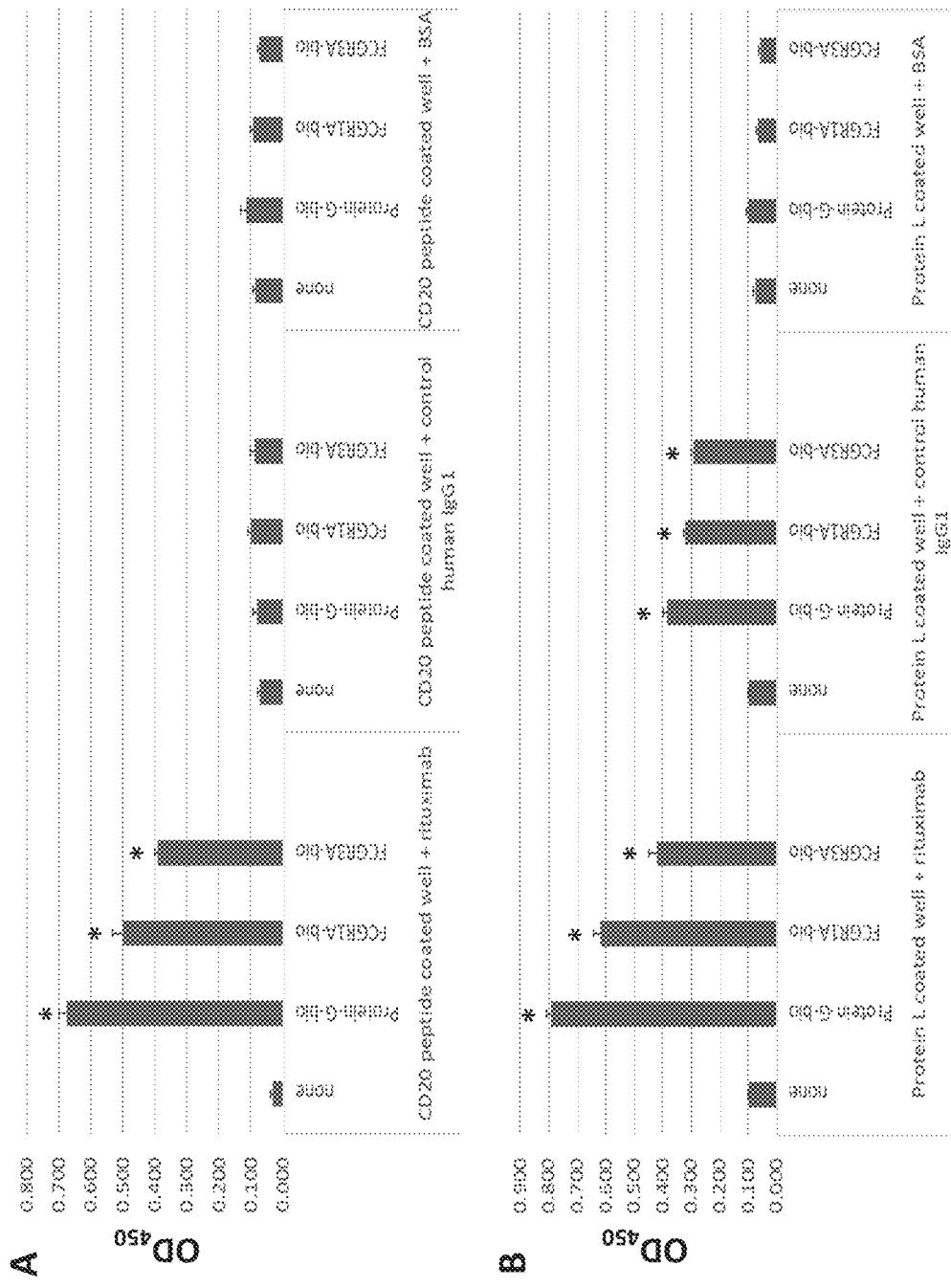

FIG. 2 provides an example of the ability of probe pairs to be used in combination with a dual-labeled test antibody by simultaneous binding without affecting antibody binding to target antigen. As shown, while some probes are compatible for simultaneous use (i.e., Protein L and Protein G or Protein A; antigen and FCGR1A), others are not (i.e., Protein L and C1q, test antibody's antigen and FCGR2A or FCGR3A), highlighting the importance of kits with defined pairs of compatible probes to measure antibody dynamic structure.

To test for compatible Fab and Fc binding pairs to said test antibody in the presence or absence of TIPS factors, probes were applied to an ELISA format using a Fab probe as capture and a Fc probe as detector. In cases where the two probes could bind test antibody in the presence of TIPS factor, an additional test was run to ensure that the probe-bound test antibody was still capable of binding its target antigen. Tests of Fab and Fc probes consisting of antibodies, antibody fragments, Fc binding proteins FCR1A, FCR2A, FCR3A, FcRn, C1q, Protein L, Protein A and Protein G were carried out in ELISA format using buffers as previously described (Kline J B, et al. Oncotarget 8:52045-52060, 2017) with the exception of probing and washing for FcRn, which was done using powdered milk and PBS buffer pH 5.5. Briefly, 96-well plates were coated with 1 µg/mL of each capture probe, test antibody or antibody specific antigen overnight in 0.05M carbonate buffer at 4° C. The next day wells were rinsed with PBS (pH 7.2) and blocked with 5% BSA in PBS for 1 hour, then washed three times in PBS. Next, test antibodies (rituximab and pertuzumab were used as positive and negative controls, respectively), [TIPS factor CA125 has been reported to bind rituximab but not pertuzumab (Kline J B et al. Eur J Immunol 48:1872-1882, 2018)] with or without CA125 and a biotinylated Fc probe were added and plates were incubated for 1 hr at room temp. Next, wells were washed in PBS and secondarily probed with streptavidin-horseradish peroxidase (SRTP-HRP) for 1 hr at room temp. Wells were then washed 3 times and TMB substrate (ThermoScientific) was added for 15 min. Reactions were stopped with 0.1N $H_2SO_4$ and plates were read at 450 nm optical density (OD) using a 96-well Varioscan plate reader. As shown in FIG. 2, the use of Protein L capture and FCGR2A, FCGR3A and Protein G probes were compatible as simultaneous Fab and Fc antibody binding was consistent and robust and test antibody was able to also bind antigen when in combination with both probes. This was demonstrated by coating ELISA plate with target antigen (CD20 peptide for rituximab and HER2 antigen for pertuzumab) and adding biotinylated rituximab or pertuzumab in the presence of Fab and Fc unlabeled proteins. Protein L and C1q pairs were not compatible. The ability of CA125 to perturb pair probe binding using Protein L as capture and biotinylated FCGR1A, FCGR2A, FCGR3A or Protein A or G as detector in the presence or absence of CA125 was then tested. As shown in FIG. 3, CA125 resulted in decreased FCGR3A binding but not FCGR1A, Protein A (not shown) or Protein G to rituximab. No effect was seen for pertuzumab as expected as CA125 does not bind pertuzumab (Kline J B, et al. Oncotarget 8:52045-52060, 2017; Gunn, et al. Mucosal Immunol 9:1549-1558, 2016). These data demonstrate that finding complementary probes that can simultaneously bind a test antibody for detection is required but not sufficient to be useful for identification of TIPS factor Sensitive Antibodies (TSAs) such as rituximab. Probes may have varying, unobvious behaviors when a test antibody interacts with a TIPS factor, making these probes less effective as screening tools to identify TSAs as well as TIPS factors and for screening for TIPS factor inhibitors. Pairs that are more stable (i.e. Protein L and Protein G; Protein L and Protein A; test antibody antigen and FCGR1A, or other probes including complementary antibody and/or aptamers Fab and Fc binding probes) may be most useful in studying the antibody dynamic structure as described and taught in Example 2 in the presence of TIPS factors.

As shown in FIG. 3, TIPS factors such as CA125 that can bind to a TSA such as rituximab, can lead to altered dynamic structure and antibody humoral function. These assays are useful for monitoring functional effects that TIPS factor and TIPS factor inhibitors may have on a dual-labeled test antibody. All biotinylated probes were created using sulfo-tag conjugation as described by the manufacturer (Meso Scale Diagnostics Inc). All reactions were done in at least triplicate and mean values were analyzed using students T-test.

Example 2—Determination of Complementary Probes to Measure Antibody Dynamic Structure of Dual-Labeled Test Antibody in the Presence or Absence of Tips Factors As shown in Example 1, it is possible to have probes bind the N-terminus/Fab domain and the C-terminus/Fc domain of a test antibody and then measure the effects of a TIPS factor to bind and alter the test antibody's dynamic structure resulting in decreased binding of low affinity Fc receptors such as FCGR2A and FCGR3A but not higher affinity binding proteins (i.e., Protein L, Protein G, FCGR1A), antibodies and/or aptamers. The latter group of probes can retain binding to test antibody in the presence of TIPS factor binding to test antibody and are useful in additional formats that can monitor the dynamic structure of test antibody by measuring its N- and C-terminal distance at steady-state and in presence of a TIPS factor to determine if the TIPS factor binds and alters the test antibody's dynamic structure. If the distance is altered by a TIPS factor, then the antibody is determined to be bound by that TIPS factor and its dynamic structure is likely altered as is the case of rituximab and CA125 regarding the decreased FCGR2A (not shown) and FCGR3A binding.

As taught here, the ability to test antibody dynamic structure to TIPS factor binding in a high throughput system offers a unique opportunity to identify those antibodies that are susceptible to TIPS factors (TIPS Susceptible Antibody, TSAs) and allows during development of a therapeutic antibody program: (1) the avoidance of patients that express a said TIPS factor to be treated with an affected TSA; (2) use of the paired probe system to screen for compounds that can overcome the susceptibility of TSA to TIPS factor(s) binding; and/or (3) the use of dual-labeled test antibodies with complementary fluorescent probes that can monitor the steady-state distance between the N- and C-terminal domains in the presence or absence of TIPS factor to either engineer a refractory TSA or develop a TIPS factor inhibitor. Any method of labeling a dual-labeled test antibody as described above can be used along with complementary fluors that can be monitored via fluorescent resonance energy transfer (FRET) in which an increased FRET signal would indicate the TIPS factor causing the test antibody's N and C-terminal ends to become closer in proximity while a decreased FRET signal would indicate the TIPS factor causing them to become more distal; in either case indicating an effect on test antibody's dynamic structure and function.

Figures 4A, 4B:
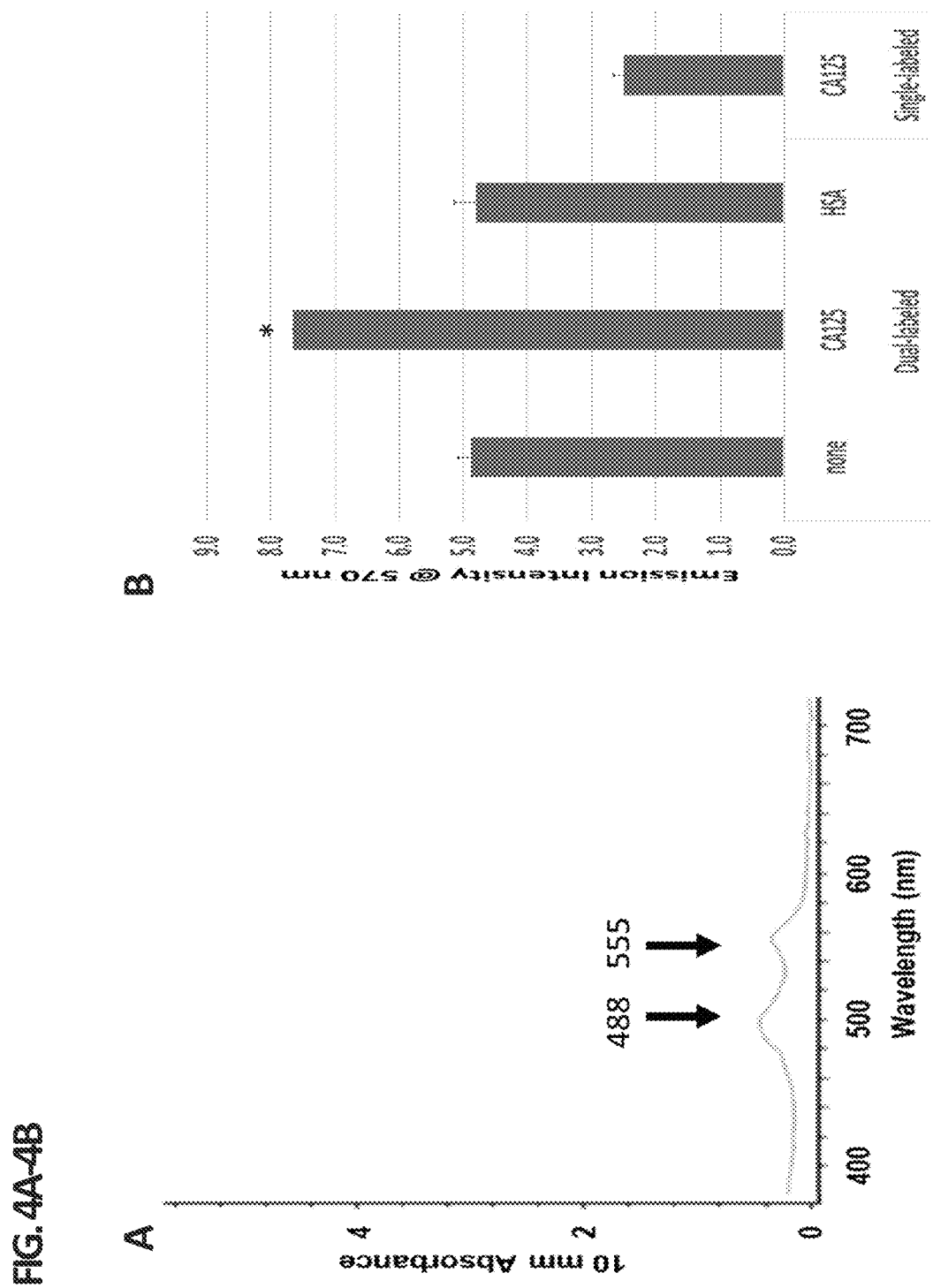
Figures 5A, 5B, 5C:
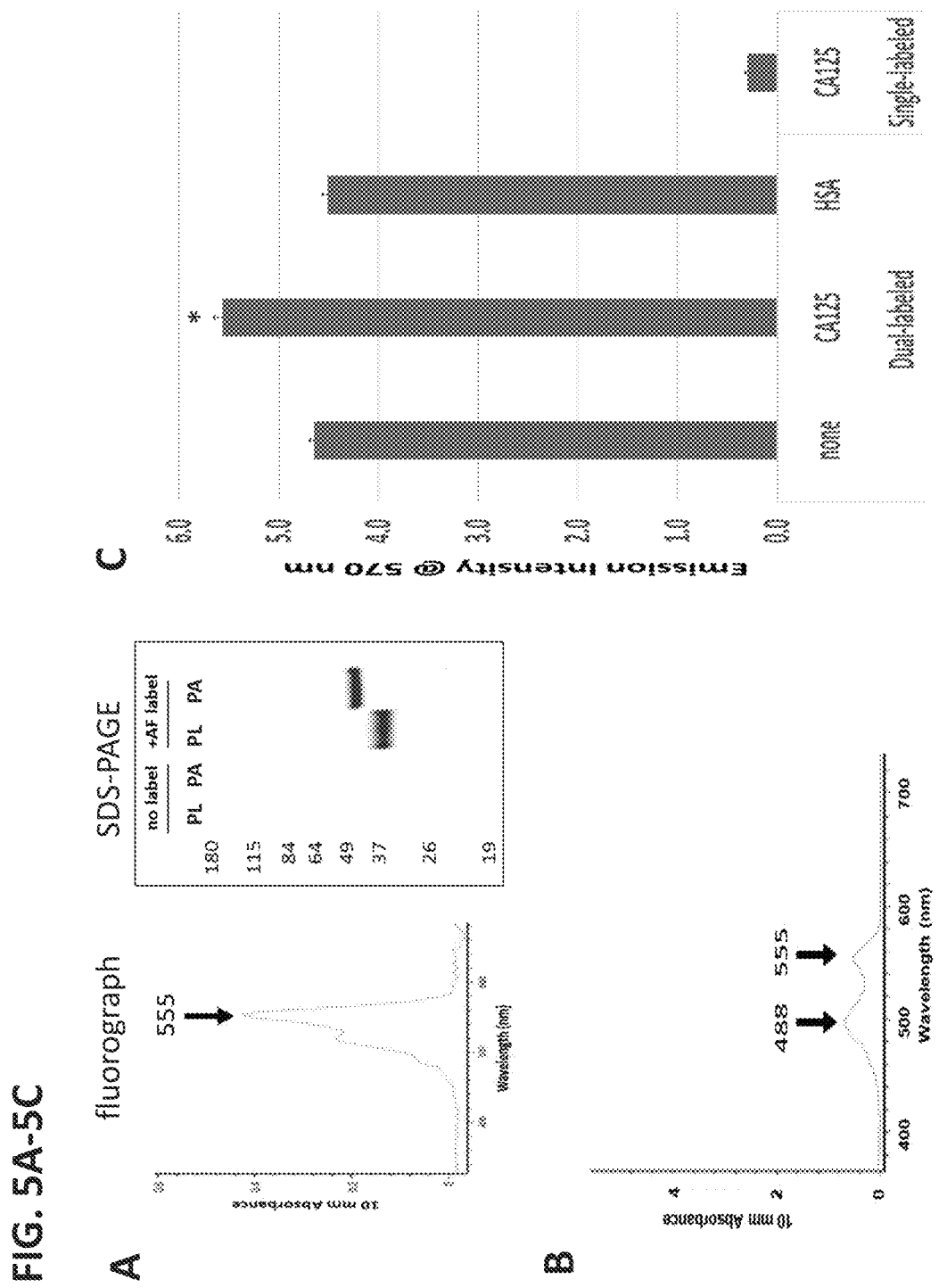

As shown in FIG. 4, a dual-labeled test antibody was formed by the binding of fluor labeled antibody probes that could specifically recognize the Fab and Fc domains of a test antibody. The anti-Fab antibody was labeled with Alexa fluor AF488 and the anti-Fc antibody was labeled with Alexa fluor AF555. Probes were simultaneously crosslinked to the test antibody using 2.5 mM disuccinimidyl suberate in 100 mM $NaHPO_4$, 20 mM HEPES, 150 mM NaCl and 100 mM $H_2CO_3/Na_2CO_3$ followed by quenching with 1M Tris-HCl, pH 7.5. Samples were desalted and purified over a protein A column, which binds the humanized test antibody but not the non-human conjugated antibody probes. The test antibody was analyzed for concentration and dual labeling via NanoDrop One™ spectrophotometry/fluorometry as recommended by the manufacturer (Thermo Scientific). As shown in FIG. 4A, a dual-labeled AF488 and AF555 test antibody was generated and used in a fluorescent resonance energy transfer (FRET) assay shown in FIG. 4B. Briefly, the Fab488-Fc555 dual-labeled or individual-labeled test antibodies were incubated with 10 ng/ml of TIPS factor CA125, human serum albumin (HSA) or buffer only in 0.05M phosphate buffer, pH 7.0 in a black 96-well opaque microplate (Greiner) and quantified via FRET using a Varioscan fluorescent plate reader in triplicate. Samples were incubated from 10 min to 3 hrs and tested for FRET activity using 470 nm excitation with a delay time of 0.05 msec, an integration time of 0.4 msec and read at an emission wavelength of 570 nm following methods previously described (Chakraborty S, et al. PLOS ONE 9:e102572, 2014). As shown, HSA had a similar value as probe in buffer alone, while the dual-labeled test antibody treated with CA125 had a 35% increase in 570 nm emission signal demonstrating an increase in FRET signal due to the N- and C-termini coming into closer proximity. These values were similar among timepoints of the experiment and represent a minimum of triplicate datapoints. The addition of single-labeled test antibody with Fab555 plus single-labeled test antibody with Fc488 resulted in no enhanced FRET signal when CA125 was added and had an overall much lower baseline signal in buffer alone than the dual-labeled antibody, 1.850 vs 4.880 at 570 nm, demonstrating the need for the two fluor dyes to be in close proximity and on the same molecule for detecting TIPS factor effect(s) on an antibody's dynamic structure.

FIG. 5, demonstrates the use of a dual-labeled test antibody formed by the binding of AF555-labeled Protein L (referred to as PL555) that specifically recognizes the Fab light chain and AF488-labeled Protein A (referred to as PA488) that recognizes the test antibody's Fc domain. The generation of PA488 proteins have been previously reported (Thermofisher.com/secondary). No previous findings have identified the attempted development of an AF555-labeled Protein L for any utility including its use as a secondary probe for AF488 paired FRET. Here we teach the generation and utility of PL555 for FRET applications. To generate PL555, 1.9 mM of recombinant Protein L (Pierce Biotechnology) was incubated with 750 μM succinimidyl ester labeled AF555 in 0.1M $Na_2CO_3$ for 1 hr. Reactions were desalted using 7 kDa molecular weight cut off (7-MWCO) Zeba columns (ThermoScientific) and Protein L-AF555 labeling was confirmed by SDS-PAGE electrophoresis/UV visualization via imaging on an I-Bright CL1000 imager (ThermoFisher) and NanoDrop One spectrophotometry/fluorometry. As shown in FIG. 5A, an AF555-Protein L labeled probe with the correct fluor spectrum of 555 nm (left figure) and molecular weight of 36 kDa (right figure) was generated. Next, a 2:1 molar volume of test antibody and PL555 and PA488 together (for dual labeling) or each alone (for single labeling) were incubated in the presence of 2.5 mM DSS as described above. Test antibodies were purified via size exclusion using a 100 kDa molecular weight cutoff (100-MWCO) dialysis tube in PBS (pH 7.0) for 72 hrs at 4° C. Antibodies were then analyzed for concentration and dual labeling as described above. Testing for antigen binding demonstrated that the dual-labeled test antibody still retained antigen binding (not shown). FIG. 5B, demonstrates that the dual-labeled test antibody was generated and was next used in fluorescent resonance energy transfer (FRET) assay using methods as described above. Results are shown in FIG. 5C. Briefly, the PL555-PA488 dual-labeled test antibody was incubated with 10 ng/ml of TIPS factor CA125, human serum albumin (HSA) or buffer only in 0.05M phosphate buffer, pH 7.0 and quantified via FRET using a 96-well Varioscan fluorescent plate reader. Samples were incubated 10 min to 3 hours and tested for FRET activity using a 470 nm excitation wavelength with a delay time of 0.05 msec, an integration time of 0.4 msec and read at an emission wavelength of 570 nm. As shown, HSA had similar value as probe in buffer alone, while test probe treated with CA125 had a 18% increase in 570 nm emission signal, demonstrating an increase in FRET signal in the presence of CA125. These values were similar among timepoints of the experiment and represent a minimum of triplicate datapoints. The addition of single-labeled test antibody labeled with PL555 plus single-labeled test antibody labeled with PA488 resulted in no FRET signal when CA125 was added and had a much overall lower baseline 0.655 vs 4.70 at 570 nm, demonstrating the need for the two complementary fluors to be in close proximity on the same molecule to detect TIPS factor binding and effect on a test antibody's dynamic structure.

As shown in FIG. 6, a dual-labeled test antibody was formed by direct conjugation to unique residues within a test antibody. The anti-CD20 antibody rituximab has been shown to be bound by CA125 that in turn suppresses its humoral immune function(s) (Kline J B et al. Eur J Immunol 48:1872-1882, 2018). Recent mapping localized the CA125 binding to the Fab region. We engineered a variant rituximab containing an unpaired cysteine (CYS) at residue 169 in the heavy chain (S169C) using a standard PCR-based random mutagenesis of the Fab domain regions. Randomized fragments were cloned into eukaryotic expression vectors, transiently transfected into mammalian host cells and functionally screened using culture supernatants to identify putative rituximab mutants that could still bind CA125 and its CD20 antigen. After screening and sequencing of hundreds of clones that retained CD20 and CA125 binding, we identified one clone that comprised the S169C mutant (SEQ ID NO: 26 and 27). This clone is referred to as RTX-169. After scale up of antibody production via larger scale transient transfection of 293 cells and protein A column purification, we prepared RTX-169 for direct cysteine labeling following methods as previously described (Banks D D, et al. J Pharm Sci 97:764-779, 2008). First, 1 mg/mL of rituximab wild type (RTX-WT) and RTX-169 were incubated with 1.5 mM L-cysteine (SigmaAldrich) in phosphate buffer saline, pH 7.0 overnight at 4° C. The next day, reactions were desalted using 7-MWCO Zeba columns and quantified for protein content via NanoDrop One. Each antibody was then tested for decysteinylation via the Ellman assay following the manufacturer's instruction (Gold Biotechnology). Analysis found a 12% enhancement of Ellman reagent labeling of treated vs untreated RTX-169 mAbs, while no difference was observed between treated or untreated RTX-WT, suggesting the presence of the free cysteine 169 within RTX-169. Both RTX-WT and RTX-169 were then treated with a 20:1 molar ratio of $NaN_3$:antibody overnight at room temp as previously described (Li, X Y. Biotechnol Prog 28:856-861, 2012) and equal molar concentrations of $NaN_3$-treated and untreated antibodies were incubated with 200 μM of dibenzylcyclooctyne-PEG4-biotin (DBCO-biotin) (Sigma Aldrich) for 1 hr at room temp to form antibody-biotin conjugates via click chemistry, a process known by those skilled in the art. Samples were desalted using 7-MWCO Zeba columns as above and tested for biotin labeling via ELISA and western blot. For ELISA, triplicate wells were plated with 0.2 mg/mL of $NaN_3$-treated or untreated, DBCO-biotin exposed RTX-WT or RTX-169 in 0.05M carbonate buffer overnight at 4° C. Wells were washed with 0.05M phosphate buffer, pH7.2 (PB buffer), blocked with 5% bovine serum albumin (BSA) in PB buffer then probed with a 1:3000 dilution of streptavidin-horseradish peroxidase (SRTP-HRP) for 1 hr at room temp. Wells were then washed with PB buffer and exposed to TMB substrate (ThermoScientific) for 5 min, stopped with 0.1N $H_2SO_4$ and read via OD at 450 nm using a Varioscan 96-well plate reader. As shown in FIG. 6A, The RTX-169 had a significantly enhanced biotin labeling than the either the $NaN_3$-untreated RTX-169 or the $NaN_3$-RTX-WT treated antibodies (P<0.000009), which was likely due to the free cysteine at residue 169 within RTX-169. To confirm labeling in the N-terminal Fab domain, RTX-169 was digested with papain and Fab and Fc fragments isolated via Protein L and Protein A agarose beads as recommended by the manufacturer (ThermoScientific). Full length RTX-169-DBCO-biotin labeled and unlabeled RTX-169 along with DBCO-biotin labeled RTX-169 Fab and Fc fragments were electrophoresed on a 4-12% non-denaturing SDS-PAGE gel, electroblotted and probed by western blot for the presence of biotin using STRP-HRP. As shown in FIG. 6B, the RTX-169-DBCO-biotin full length and Fab fragment both bound SRTP-HRP while the untreated RTX-169 and Fc-fragment of the DBCO-biotin labeled RTX-169 did not, confirming biotin specific labeling within the RTX-169-DBCO-biotin Fab domain. We next used the DBCO-biotin tag on RTX-169 to label RTX-169 with Alexa fluor AF555. RTX-169-DBCO-biotin was incubated with an avidin-labeled AF555 and PA488 at a 2:1 ratio for 1 hour in the presence of DSS as described above. Antibody was purified via dialysis using a 100-MWCO dialysis membrane and analyzed by a denaturing SDS-PAGE gel that showed high molecular weight species as expected for RTX-169-AF555-PA488 dual-labeled antibody (not shown). The test antibody was further analyzed by NanoDrop One spectrophotometry/fluorometry and confirmed to be dual labeled with the AF488 and AF555 fluors (FIG. 6C). Antigen binding of the dual-labeled antibody was confirmed via ELISA (not shown). The test antibody was then used in FRET using similar parameters as above in the presence of buffer, HSA or CA125 and quantified for 10 min to 3 hrs. As shown in FIG. 6D, the RTX-169-AF555-PA488 antibody showed a positive FRET signal when incubated with CA125 in contrast to HSA or buffer alone, confirming the utility of this format to detect TIPS factor binding to TSAs such as rituximab.

The teachings of the compositions of reagents and the methods for their use to uncover TSAs and TIP factors enables the utility to use specific binding of probes such as but not limited to anti-Fab or anti-Fc antibodies, Protein A, G or L binding proteins, Fab and/or Fc binding aptamers as well as single amino acid changes within the Fab and/or Fc domains to form dual-labeled test antibodies. The formation of such dual-labeled test antibodies using any combination of complementary fluor pairs or other detector agents as discussed above is suitable for identifying potential TIPS factors that can bind test antibodies, identifying TSA affected antibodies, and their use for screening chemical and protein libraries for TIPS factor inhibitors as novel therapies as well as using TIPS expression profiles for patient selection.

We claim:

1. A method for characterizing an antibody comprising a Fab and a Fc domain, comprising:
    contacting a first fluor-labeled protein L (SEQ ID NO: 1), and a second fluor-labeled protein A (SEQ ID NO: 2), with the antibody to be characterized to form a ternary complex, wherein the first fluor-labeled protein L binds to the Fab domain and the second fluor-labeled protein A binds to the Fc domain, wherein the first and second fluors participate in FRET, wherein the antibody to be characterized is an anti-tumor antibody obtained from a cancer patient;
    determining fluorescence resonance energy transfer (FRET) of the ternary complex;
    contacting the ternary complex or components of the ternary complex with tumor-induced or -produced factor (TIPS factor) Cancer Antigen 125 (CA125); and
    determining FRET of the ternary complex in the presence of the TIPS factor.

2. A method of screening test substances for the ability to mitigate an effect of tumor-induced or -produced factor (TIPS factor) Cancer Antigen 125 (CA125) on TIPS-susceptible antibody selected from the group consisting of rituximab, trastuzumab, cetuximab, YP219, trastuzumab emtansine, ocrelizumab, daratumumab, elotuzumab, alemtuzumab, necitumumab, pertuzumab, obinutuzumab, nivolumab, ipilimumab, pembrolizumab, ofatumumab, panitumumab, ibritumomab tiuxetan, sacituzumab govitecan, brentuximab vedotin and tositumomab, comprising a Fab domain and a Fc domain, the method comprising:
    contacting the TIPS-susceptible antibody with (a) a first fluor-labeled protein L (SEQ ID NO: 1), that specifically binds to the Fab domain of the TIPS-susceptible antibody, and (b) a second fluor-labeled protein A (SEQ ID NO: 2) that specifically binds to the Fc domain of the TIPS-susceptible antibody, to form a first complex;
    contacting the first complex with (c) the TIPS factor, to form a second complex;
    contacting at least some of the second complex with (d) a test substance; and
    measuring fluorescence resonance energy transfer (FRET) of the first complex, the second complex in the absence of the test substance, and the second complex in the presence of the test substance.

* * * * *